United States Patent [19]

Streber et al.

[11] Patent Number: 6,153,401
[45] Date of Patent: Nov. 28, 2000

[54] MICROORGANISMS AND PLASMIDS FOR 2, 4-DICHLOROPHENOXYACETIC ACID (2,4-D) MONOOXYGENASE FORMATION AND PROCESS FOR THE PRODUCTION OF THESE PLASMIDS AND STRAINS

[75] Inventors: Wolfgang R. Streber, Berlin, Germany; Kenneth N. Timmis, Chambefy, Switzerland; Meinhart H. Zenk, Munich, Germany

[73] Assignee: Hoechst Schering AgrEvo GnbH, Frankfurt am Main, Germany

[21] Appl. No.: 07/322,604

[22] Filed: Mar. 10, 1989

Related U.S. Application Data

[63] Continuation-in-part of application No. PCT/DE87/00392, Aug. 28, 1987.

[51] Int. Cl.[7] .................................................. C12N 15/31
[52] U.S. Cl. ................. 435/69.1; 435/252.3; 435/320.1; 435/410; 536/23.7; 800/205
[58] Field of Search ............................... 435/69.1, 252.3, 435/172.3, 320.1; 536/27; 935/92

[56] References Cited

U.S. PATENT DOCUMENTS 4,349,629  9/1982  Cary et al. .............................. 435/172

OTHER PUBLICATIONS

Nature 317: 741–744, Oct. 24, 1985, Comai et. al. Expression in plants of a mutant aro A gene from Salmonella typhimurium confers resistance to glyphosate.

Appl. Env. Micro. 49(5) : 1237–1245, May 1985, Amy et al. Characterization of Aquatic Bacteria and Cloning of Genes Specifying Partial Degradation of 2,4–Dichlorophenoxyacetic acid.

J. of Bact. 162C1 : 102–105, Apr. 1985, Beguin et al. Sequence of a Cellulase Gene of the Thermophilic Bacterium Clostrilium Thermocellum.

R.H. Don et al., J. Bacteriol. 145 681 (1981).
R.H. Don et al., J. Bacteriol. 161 416 (1985).
R.H. Don et al., J. Bacteriol. 161 85 (1985).

*Primary Examiner*—John Ulm
*Attorney, Agent, or Firm*—Frommer Lawrence & Haug

[57] ABSTRACT

The disclosure relates to the production and the use, by genetic engineering, of plasmids and bacterial strains containing, on a short, precisely characterizable DNA segment, the gene tfda or a gene almost identical to tfdA. The novel plasmids and microorganisms are suitable for the production of 2,4-D (2,4-dichlorophenoxyacetic acid)-monooxygenase, and as starting materials for the transfer, by genetic engineering of the 2,4-D-degrading property of this enzyme to various organisms.

16 Claims, 17 Drawing Sheets

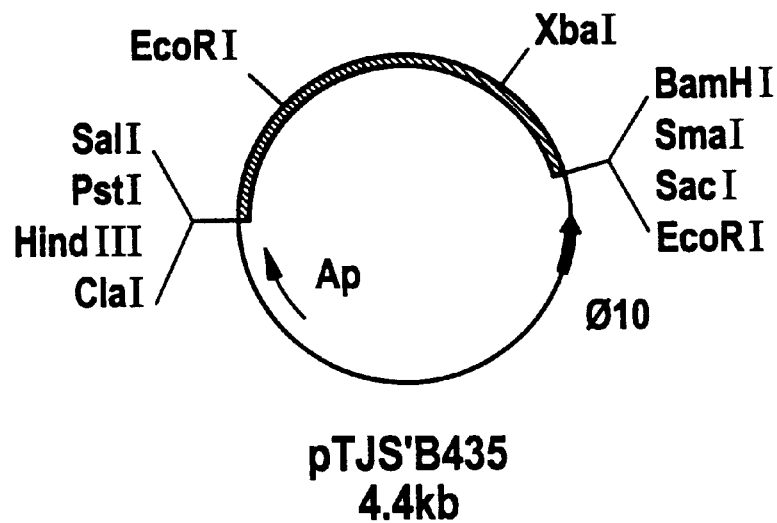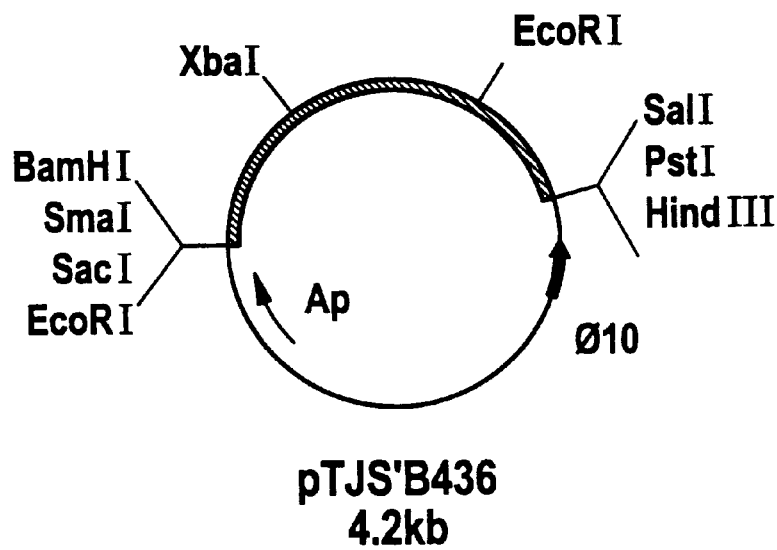
Fig. 6
pTJS'B435
4.4kb
pTJS'B436
4.2kb

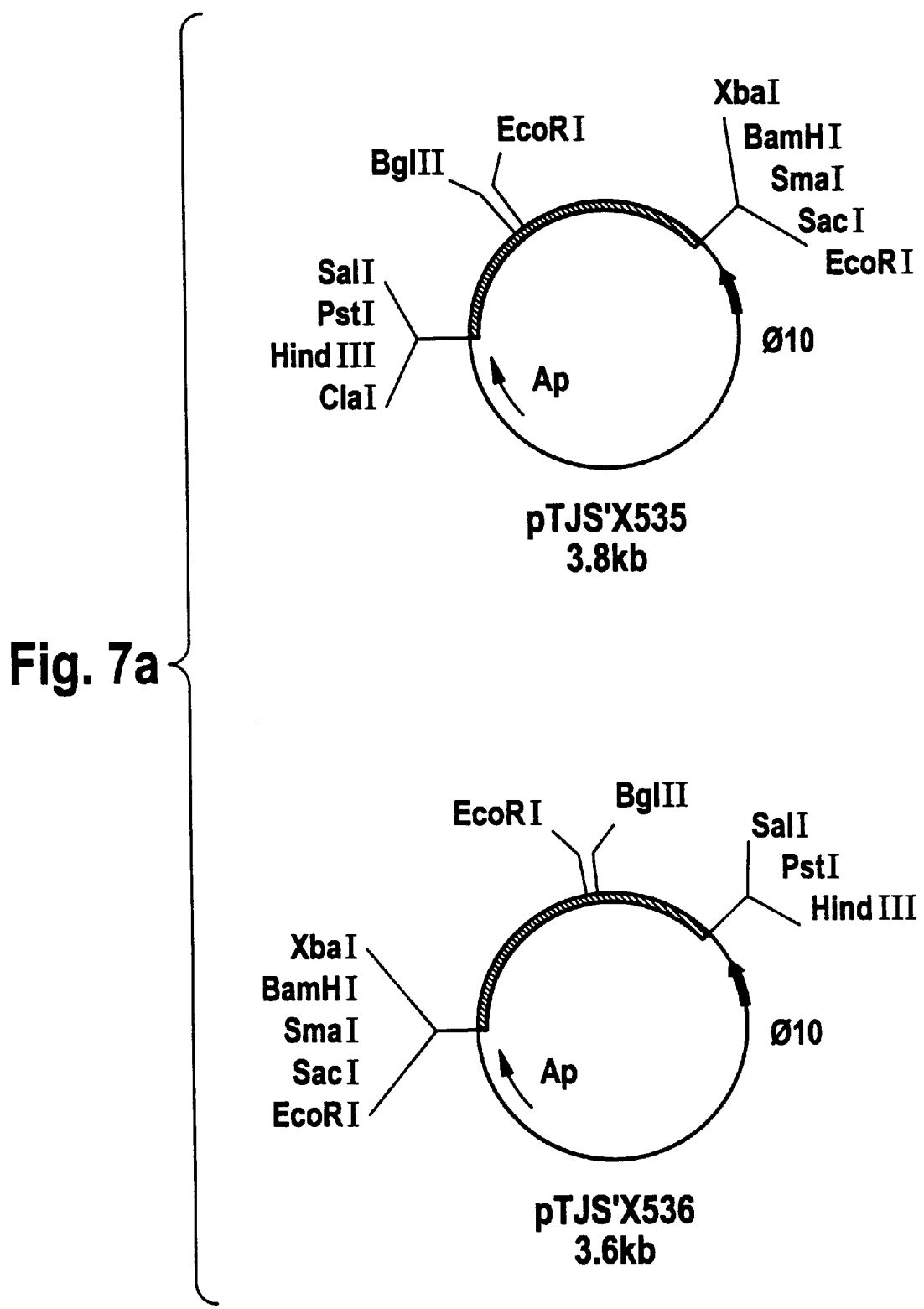

Fig. 10a-1

```
         10         20         30         40         50         60
GGATCCTGTCTCAGCTGGGCGGCCCAATGCTCGAACCCGCTCGATATACAGCCGTTCGTAG 70         80         90        100        110        120
TGCAGGTGCTCCACCGTGATTCCAGGCTCCTGGGGTAGAAGCGGGCCGACACCGAGATGG 130        140        150        160        170        180
ATGGCCGGCACGCAGGCCTCGATCTGCCGCACCTTGGGCATCAGGGCCAGAGACAGC 190        200        210        220        230        240
GTCGCCCCGGGACCCGCCTGCGTGAACGCAATGGAGCAATGCCGGGACGGTCTGGTAGATC 250        260        270        280        290        300
GCCGTGCCGAGGTAGCCGATATCGAGTTGGCCGATCTCGCCCCGGCTGGGCGGCGGGAC 310        320        330        340        350        360
CGGTCCACGGAAGTCCGACCCAGTTCGAGCATGCGCCGTGCATCTTCGAGAAACGCGGGCC 370        380        390        400        410        420
GCGGCGGGCGTGAGCTGCACGCCGCCGCTCGAACAACAACGCCCCAGATGC 430        440        450        460        470        480
TGTTCGAGCCGTGAATCTGTGTCGGCTGGGAAAATATGCAGCCGCCGCG 490        500        510        520        530        540
GCGGCACCGACGTTGCCCTCCTCCCGGCAGCAACGAAATAGCGAAGCTGTCGAAACTCC
```

Fig.10a-2

```
550         560         570         580         590         600
ATTCTTCACTCCCTGGTGGCTGGGCTCCGGGCTGCCGGGAGAGCCATACCGATCCCGTATCGCT 610         620         630         640         650         660
CGCGCTGATGGAAGGTATTAGACCATATGGCCCCGGCATTTCTAGACTACCGCCATGATAA 670         680         690         700         710         720
AACTCGGGCTGCTCTCTCGTCTCTGCTGGAACATCTTCAGGCGCGCTGAGCCGTCTTTTGAA 730         740         750         760         770         780
ACAGTCTCTTAGAAAAGGAGCAAAAAAGTGAGCGTCGTCGCAAATCCCCTTCATCCCTCTT 790         800         810         820         830         840
TTCGCCGCAGGGGTCGAAGACATCGACCTTCGAGAGGCCTTGGGTTCGACCGAGGTCCGA 850         860         870         880         890         900
GAGATCGAACGGCTAATGGACGAGAAGTCGGTGGTGTTCCGGGGGCAGCCCCTGAGT
```

Fig.10a-3

```
        910        920        930        940        950        960
CAGGATCAGCAGATCGCCTTCGCGCGCAATTTCGGGCCACTCGAAGGCGGTTTCATCAAG 970        980        990       1000       1010       1020
GTCAATCAAAGACCTTCGAGATTCAAGTACGCGGAGTTGGGACATCTCGAACGTCAGT 1030       1040       1050       1060       1070       1080
CTCGACGGCAAGGTCGCGCAACGCGATGCGCGCGAGGTGTCGGAACTTCGGAACCAG 1090       1100       1110       1120       1130       1140
CTCTGGCACAGCCGACAGCTCCTTTCAGCAACCTGCTGCCCGCTACTCGATGCTCTCCGCG 1150       1160       1170       1180       1190       1200
GTGGTGGTTCCGCCCGTCGGGCGCGACACCGAGTTCTGCGACATGCGTGCGGGCATACGAC 1210       1220       1230       1240       1250       1260
GCGCTCCCTCGGGACCTCCAATCCGAGTTGGAAGGGCTGCCTGCCGAGCACTACGCACTG
```

Fig.10b-1

```
              1270      1280      1290      1300      1310      1320
AACTCCCGGCTTCCTGCTCTCGGCGACACCGACTATTCGGAAGGCGCAACGCAATGCCATGCCG 1330      1340      1350      1360      1370      1380
CCGGTCAACTGGCCGCTGGTTCGAACCCACGCCCGGGCGCTCCGGGCCAAGTTTCTCTTCATC 1390      1400      1410      1420      1430      1440
GGCGCGCACGCGAGCCACGTCGAAGGCCTTCCGGTGGCCGAAGGCCGGATGCTGCTTGCG 1450      1460      1470      1480      1490      1500
GAGCTTCTCGAGCACGGCGACACAGCGGGAATTCGTGTACCGGCATCGCTGGAACGTGGGA 1510      1520      1530      1540      1550      1560
GATCTGGTGATGTGGGACAACCGCTGCGTTCTTCACCCGGGACGCAGGTACGACATCTCG 1570      1580      1590      1600      1610      1620
GCCAGGCGTGAGCTGCGCCGGGCGACCACCCTGGACGATGCCGTCGTCTAGCGCACGCCA 1630      1640      1650      1660      1670      1680
TGGGCGCACGCCCTTTTCGCGAAGGCCCCACAAGATGTACGCAACCCTGATCAGCGGCAGC
```

Fig.10b-2

```
     1690       1700       1710       1720       1730       1740
CGTAGCCTGGACGGGCGACACCCTTGGCGCAGCGCGTCCTTCGAGCGCGGGGCGGCCTGGCG 1750       1760       1770       1780       1790       1800
GCATGGGGATTGAGGCCCGGTCGTCGCCGGTGATGTCGCCATCCTCATGCGCAATGACTTTCCGGTG 1810       1820       1830       1840       1850       1860
CTCGAAATGACGCTGGCCGCGAACCGCGGCATCGTTGCGGTTGCCTTTGAACTGGCAT 1870       1880       1890       1900       1910       1920
GCGAACCGGGACGAGATCGCCCTTCATCCTCGAGGACTGCAAAGCGCGTGTGCTCGTCGCG 1930       1940       1950       1960       1970       1980
CACACCGATCTGCTCAAGGGGCGTTGCATCCGGGTGCCCGAGGCCTGCAAGGTGCTGGAA 1990       2000       2010       2020       2030       2040
GCCGCGTCGCCCGCCCCGAGATCCGGCAGGCCTATCGGCCTGTCCGATGCGTCGTGCACGGGCG

2050
AACCCGGGCACGGGTCGAC
```

Fig. 12a
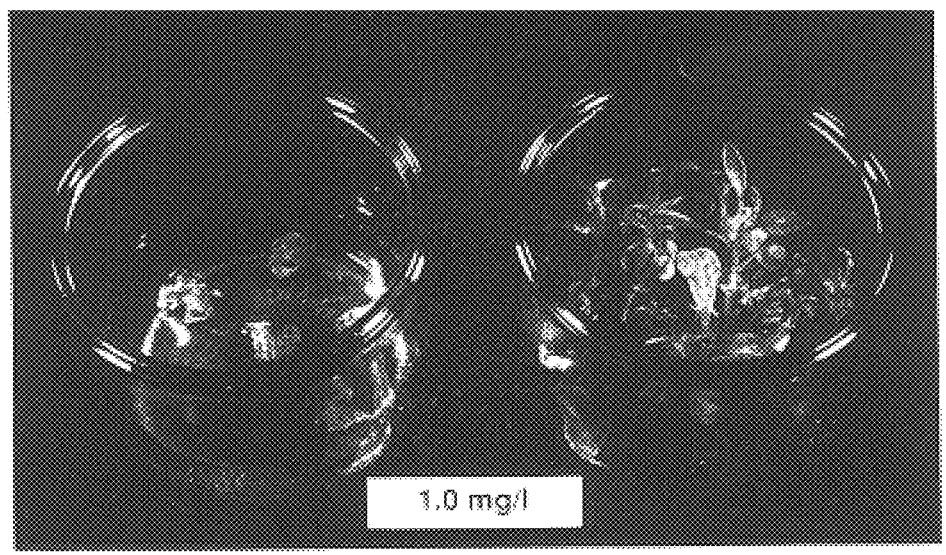
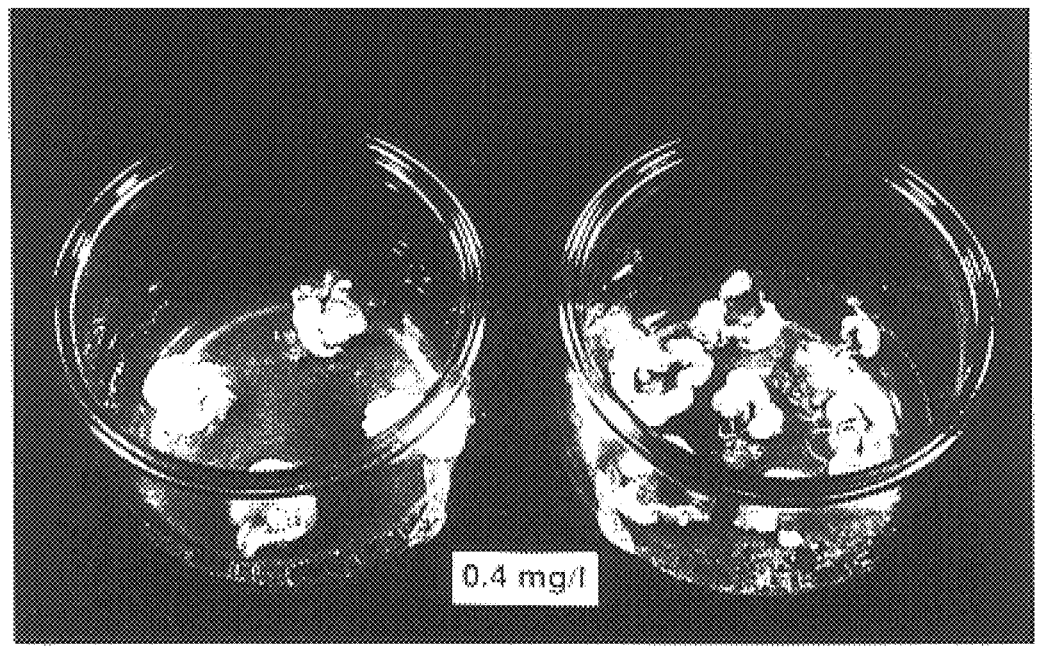
Fig. 12b

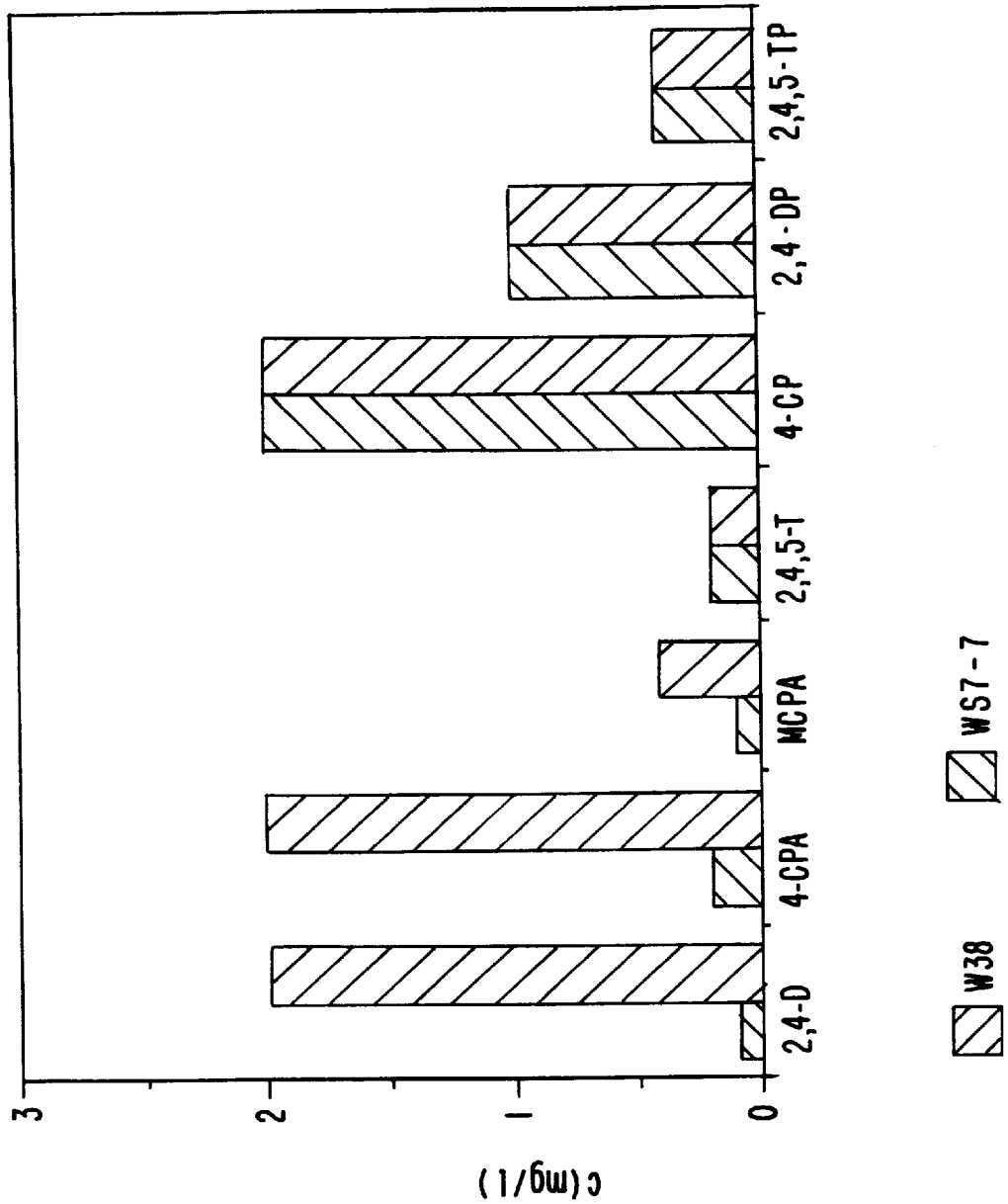

MICROORGANISMS AND PLASMIDS FOR 2, 4-DICHLOROPHENOXYACETIC ACID (2,4-D) MONOOXYGENASE FORMATION AND PROCESS FOR THE PRODUCTION OF THESE PLASMIDS AND STRAINS

This is a continuation-in-part of PCT Application No. PCT/DE87/00392, filed Aug. 28, 1987.

BACKGROUND OF THE INVENTION

The present invention relates to the production, by genetic engineering, of plasmids and bacterial strains containing the gene tfdA, or a gene essentially identical to tfda, on a short, exactly characterizable DNA segment. The novel plasmids and microorganisms are especially well suited for the production of 2,4-D-monooxygenase, as well as for serving as starting compounds for the genetically engineered transfer of the 2,4-D-degrading properties of this enzyme to various organisms (including the thus-attainable 2,4-D-tolerance in genetically transformed plants).

2,4-D-Monooxygenase is an enzyme catalyzing in many 2,4-D-degrading organisms the first step in the metabolizing of 2,4-dichlorophenoxyacetic acid (2,4-D). Among the 2,4-D-degrading organisms belong, in particular, soil bacteria, such as, for example, Acinetobacter, Alcaligenes, Arthrobacter, Cyronebacterium and Pseudomonas [compare, in this connection, G. R. Bell, Can. J. Microbiol. 3 : 821 (1957); J. M. Bollag et al., J. Agric. Food Chem. 16 : 826 (1968); R. H. Don et al., J. Bacteriol. 145 : 681 (1981); W. C. Evans et al., Proc. Biochem. Soc. Biochem. J. 57 : 4 (1954); W. C. Evans et al., Biochem. J. 122 : 543 (1971); R. P. Fisher et al., J. Bacteriol. 135 : 798 (1978); T. I. Steenson et al., J. Gen. Microbiol. 16 : 146 (1957); J. M. Tiedje et al., J. Agric. Food Chem. 17 : 1080 (1969); J. E. Tyler et al., Appl. Microbiol. 28 : 181 (1974); J. M. Tiedje et al., J. Agric. Food Chem. 17 : 1021 (1969)]. They play a significant part in the detoxification of the soil and of the wastewaters from halogenated aromatic compounds as they occur especially among the agriculturally utilized pesticides and herbicides.

In the group of the 2,4-D-degrading wild-type bacteria, the strain *Alcaligenes eutrophus* JMP134 is the most well-known and best-characterized. This strain harbors- the plasmid pJP4 having a size of about 80 kilobases and containing all of the genes important for degradation of 2,4-D (R. H. Don et al., loc. cit.). The plasmid pJP4 has also been isolated and characterized recently [R. H. Don et al., J. Bacteriol. 161 : 466 (1985)].

Five genes participating in 2,4-D degradation, denoted as tfdB, tfdc, tfdD, tfdE and tfdF, were localized by transposon mutagenesis and cloned in *E. coli*. R. H. Don et al. [J. Bacteriol. 161 : 85 (1985)) succeeded in attributing enzyme function to four genes by biochemical studies. However, thus far attempts have been unsuccessful regarding localizing of gene tfda on the plasmid pJP4 or on a subfragment of the latter, and to isolate this gene and to clarify its structure.

SUMMARY OF THE INVENTION

It has now been possible for the first time thanks to the present invention to isolate, to clone, and to characterize the gene tfdA. It has thus become possible to make this gene available for transfer to other organisms with the objective of expressing the tfdA-encoded 2,4-D-monooxygenase in these organisms. The latter includes microorganisms, as well as higher organisms, such as, for example, plants.

The controlled transfer of tfdA to other microorganisms offers the possibility of broadening the spectrum of compounds degradable by these organisms. As far as bacteria are concerned, transfer and expression of genes of the entire 2,4-D degradation has been disclosed in J. Bacteriol. 145 : 681 (1981) and in Arch. Microbiol. 134 : 92 (1983). However, no attempt has-as yet been made to express an isolated tfdA gene in gram-negative bacteria, such as Pseudomonas or Alcaligenes.

No known attempt has been made in connection with plants, either. Metabolism of 2,4-D by several types of plants has been reported by various sources [Weed Science 24 : 557 (1976) and Z. Pflanzenphysiol. 110 : 395 (1983)]. In lower concentrations, this compound acts as an auxin-analog plant hormone and therefore is utilized in cell culturing technique; at higher concentrations, it acts on the plant cell as well as on the entire plant in the manner of a growth inhibitor, which is the reason why it is utilized as a herbicide. In a haploid cell suspension culture of *Nicotiana silvestris,* adaptation to rising concentrations of 2,4-D brought about tolerance with respect to this synthetic growth compound based on an increased rate of metabolism [M. H. Zenk, 1974, Haploids in Physiological and Biochemical Research, in Haploids in Higher Plants. Advances and Potential; Proceedings of the First International Symposium, Guelph, Ontario, Canada, p. 339].

The tfdA gene codes for 2,4-D-monoamine oxygenase, a polypeptide having the biological activity of bringing about the cleavage of the side chain of 2,4-D; therefore, the ability to inactivate 2,4-D can be transferred, with the aid of the gene obtained from bacteria, to all those plants lending themselves to such a manipulation by genetic engineering. Methods for transferring foreign genes to plants and their progeny are already known for several types of plants (M. De Block, L. Herrera-Estrella, M. Van Montagu, J. Schell, and P. Zambryski, Expression of Foreign Genes in Regenerated Plants and in Their Progeny, EMBO J. 3 : 1681; as well as R. D. Shillito, M. W. Saul, J. Paszkowski, M. Muller, and J. Potrykus, 1985, High Efficiency Direct Gene Transfer to Plants, Bio/technology 3 : 1099).

Great hopes are harbored for the genetic transformation of plants, especially regarding the production of novel useful plants important to man [J. L. Marx, 1985, Plant Gene Transfer Becomes a Fertile Field, Science 230 : 1148]. In this context, the gene tfdA provides the availability of a novel, genetically transferable and in vivo selectable property in the form of tolerance against a growth inhibitor, as, has been known heretofore merely for a few tolerances against antibiotics and, respectively, herbicides [R. T. Fraley et al., 1983, Expression of Bacterial Genes in Plant Cells, Proc. Natl. Acad. Sci. USA 80 : 4803; and Nature 317 : 741 (1985)].

The present invention, thus provides a heretofore unknown mutant using a conventional mutation method, from a bacterial strain capable of utilizing 2,4-D as the growth substrate, such as, for example, Alcaligenes eutrophus JMP134, the structural gene for 2,4-D-monooxygenase being inactivated in this mutant. This mutant is used, employing the known methods of DNA recombination in vitro, of transformation with recombinant DNA, and of conjugative transfer of DNA, for the selection of recombinant DNA containing tfdA or genes substantially identical to tfdA.

Another aspect of this invention relates to plasmids containing the gene tfda or genes substantially identical to tfda (e.g., hybridizing with the gene of this invention and coding for a protein which has the biological activity of the protein encoded by tfda, e.g., its 2,4-D-monooxygenase activity), as well as plasmids containing parts of these genes including the promoter region.

A third aspect of this invention is to provide novel bacterial host/plasmid strains which can be used to produce 2,4-D-monooxygenase, or which can be used to transfer the 2,4-D-monooxygenase gene to other organisms.

A fourth aspect of this invention is the creation of transgenic organisms, preferably microorganisms and plants, which are resistant to the growth inhibiting effects of certain substituted or unsubstituted phenoxyacetic acids.

The plasmids of this invention can be produced by digesting DNA from wild-type bacteria exhibiting genes for metabolizing 2,4-D or compounds similar to 2,4-D with restriction endonucleases and coupling the thus-obtained DNA fragments, with the aid of a DNA ligase, with a plasmid vector which latter has previously been converted into its linear form by the same restriction enzyme.

Among the thus-formed recombinant plasmids, the tfda-containing plasmids according to this invention can be identified by introducing the plasmids into bacterial strains from which then the tfdA-containing clones can be directly selected based on a tfda-conveyed ability.

Such bacterial strains have the property of being able to exploit as sources of carbon and energy the products formed in an enzymatic reaction in vivo by 2,4-D-monooxygenase, but not the substrates thereof.

Examples of strains having the aforementioned ability are the tfda mutants according to this invention wherein all genes are active for degradation of 2,4-dichlorophenol, furthermore the strain Alcaligenes eutrophus JMP222 which exhibits degradation pathways for phenol, as well as Pseudomonas sp. B13 which can utilize 4-chlorophenol. However, a series of further bacterial strains which can degrade differently substituted phenols and are encountered primarily among the group of gram-negative bacteria can conceivably be recipients for the selection and identification of cloned tfda genes.

Preferred cloning vectors are plasmids having a wide host range, capable of replicative growth even in bacterial strains other than *E. coli*. However, plasmids capable of multiplying their DNA or parts of their DNA by integration into the genome of the host cell can like-wise be used for this purpose.

A suitable process for introducing DNA into the living cells of the aforementioned bacterial strains is, first of all, the direct transformation of these strains insofar as methods therefor are known. Thus, transformation methods exist, for example, for Pseudomonas and related gram-negative bacteria (A. A. Mercer and J. S. Loutit, 1979, Transformation and Transfection of Pseudomonas aeruginosa: Effects of Metal Ions, J. Bacteriol. 140 : 37–42; A. M. Chakrabarty, J. R. Mylroie, D. A. Friello, and J. G. Vacca, 1975, Transformation of *Pseudomonas putida* and *Escherichia coli* with Plasmid-Linked Drug-Resistance Factor DNA, Proc. Natl. Acad. Sci. USA 72 : 3647–3651]. In contrast thereto, a procedure which is applicable to all gram-negative bacteria and is substantially more effective is the transformation of an *E. coli* strain according to a method known from the literature with subsequent conjugative transfer of the plasmids into the respective bacterial strains.

Mobilizable plasmid vectors are used with preference for the conjugative transfer of cloned DNA. The genes required for transfer are made available in this case either by so-called helper plasmids or by mobilizing strains specifically designed for this purpose.

The plasmids containing tfda can be isolated according to known methods as unequivocally definable chemical compounds from the aforesaid bacterial strains obtained directly by selection on suitable growth substrates or from clones of *E. coli* identified by the aforementioned method or by other conventional testing systems as regards expression of tfdA.

The advantage of direct selection of tfdA-containing strains by a growth test resides, above all, in that it permits, in contrast to the previously known methods all of which are based on relatively expensive enzyme tests, the identification of a tfdA-containing plasmid among a very large number of various plasmids as they are produced with preference in the preparation of gene banks, i.e. the randomized cloning of DNA fragments of genomic DNA. The advantage thus resides in broad applicability of the process, for cloning of tfdA genes is thus no longer restricted to wild-type strains carrying the gene tfdA on a readily isolable plasmid, but rather is made possible from almost all wild-type strains, even those containing the gene on a poorly accessible plasmid or on the chromosome.

The plasmids of this invention are obtained, for example, by cutting the plasmid pJP4, stemming from Alcaligenes eutrophus JMP134, on which the genes lie for degrading 2,4-D, with the restriction endonuclease HindIII, separating the thus-formed DNA fragments by electrophoresis, and linking the individual isolated fragments with the HindIII-cut and dephosphorylated vector pVK101. The mobilizing strain *E. coli* S17-1 is transformed with the recombinant DNA, and plasmid-containing strains are selected on a tetracycline-containing medium. From strains containing recombinant plasmids identified by restriction analysis, the plasmid DNA is transferred by conjugation to the above-mentioned tfdA mutant JMP134:Tn5-2, and expression of the cloned tfda gene is confirmed by growth of the host strain on 2,4-D-containing minimal medium. In this way, the plasmid pVJH21 can be identified containing the gene tfdA on a HindIII fragment having a size of 21 kilobases, stemming from pJP4. The identity of the cloned fragment can be confirmed by isolation of the plasmid and subsequent restriction analysis.

The plasmids according to this invention can furthermore be prepared by subcloning from recombinant plasmids containing the gene tfda. For this purpose, these plasmids are digested with one or several restriction endonucleases and the thus-formed fragments are linked with the aid of a DNA ligase with a vector plasmid that has been converted into its linear form with the same restriction endonucleases. Plasmids that contain tfdA can be selected from the thus-formed plasmids in the way described above.

Thus, for example, the plasmid pGJS3 can be produced by linking DNA fragments of the plasmid pVJH21, formed with SacI, with the SacI-cut vector plasmid pGSS33. Among the number of newly combined plasmids, those can be selected which contain an intact tfdA gene by transferring the recombinant plasmid DNA first by transformation into the mobilizing strain *E. coli* S17-1 and then from there by conjugation into the tfdA mutant JMP134:Tn5-2. By selection on 2,4-D-containing medium, plasmids are identified which contain a SacI insert having a size of 3 kilobases, the origin of which can be clearly traced back by restriction analysis to the HindIII fragment, having a size of 21 kilobases, from pVJH21,and thus to pJP4.

By subcloning DNA segments containing tfda, those plasmids according to the invention can also be produced which differ in the type of plasmid vectors utilized, in dependence on the pursued target of usage.

Thus, for example, the 3-kilobase SacI fragment from pGJS3 can be transcloned into the vector pKT231, thus forming the plasmids pKJS31 and pKJS32, offering as contrasted to pGJS3 advantages for the further characterization of tfdA due to a more favorable restriction map and the kanamycin resistance well expressed in many gram-negative bacteria. A preferred method for confirming tfdA expression by pKT231-derived plasmids as described hereinbelow is the conjugative transfer from E. coli S17-1 into the strain Alcaligenes eutrophus JMP222 with subsequent testing for utilization of phenoxyacetic acid as the growth substrate. This system has the advantages over the tfdA mutants that in this recipient strain the conjugative transfer takes place at higher efficiency and, in the kanamycin resistance, a further selectable marker is made available.

By subcloning, tfda-containing DNA fragments can also be incorporated into expression vectors on which tfda genes are expressed with the aid of a foreign (heterologous) promoter.

Thus, it is possible, for example, to incorporate the 2.8 kilobase sized SacI/SalI fragment, the 2.0 kilobase sized BamHI/SalI fragment, and the 1.4 kilobase sized XbaI/SalI fragment into the expression vectors pT7-5 and pT7-6 directly adjoining a phage promoter by means of which gene expression can be activated in a controlled fashion with the aid of a promoter-specific RNA polymerase. The tfda gene product expressed by the recombinant plasmids pTJSS'035, pTJS'B435 and pTJS'X535, the production of which will be described in Examples 8, 9 and 10, can be identified by specific labeling with radioactive methionine and subsequent gel electrophoresis. The system can furthermore be used for producing, in an E. coli strain, large amounts of 2,4-D-monooxygenase, which substantially facilitates purification and subsequent protein-chemical and enzymatic characterization of the gene product as compared with its isolation from the wild-type strain whereby additional biotechnological usage possibilities become accessible to research.

Subcloning of tfdA-containing DNA fragments in phage vectors of the type of the M13 phage makes it possible to produce single-stranded DNA. The latter can be utilized for determining the base sequence according to the method of Sanger (F. Sanger, S. Nicklen, and A. R. Coulson, 1977, DNA Sequencing with Chain-Terminating Inhibitors, Proc. Natl. Acad. Sci. USA 74 : 54631; it can furthermore serve for the controlled mutagenesis of individual bases by means of oligonucleotides, a conventional method permitting the production of restriction scission sites in a gene or the alteration of the amino acid sequence. The insertion of restriction sites in genes broadens the possibilities of application of the latter because cutting sites are thereby created for the incorporation of foreign promoters and the linkage of gene fragments for the formation of fusion proteins, as they are required, for example, for the expression of prokaryotic genes in eukaryotes.

Subcloning of the 2.8-kilobase SacI/SalI fragment from pKJS32 into the phage vectors M13tg130 and M13tg131, as described in Example 16, represents a possibility for making the gene tfda accessible to sequencing. By modification of the double-stranded DNA of the recombinant phages MJSS'030 and MJSS031, additional alterations can be performed on the insert DNA.

The plasmids according to this invention can furthermore evolve by modification from tfda-containing plasmids. By treating such plasmids with one or several restriction endonucleases, optional treatment with exonucleases, and subsequent reassembly of the DNA ends to an annular molecule, deleted plasmids are obtained, i.e. plasmids reduced in size by a specific DNA segment, which can contain a furthermore intact tfda gene.

Thus, it is possible, for example, by the removal of defined DNA fragments from the plasmids pKJS31 and pKJS32, to shorten the insert contained therein, having a size of 3 kilobases, on one side, up to the XbaI scission site and, on the other side, up to the SalI scission site, without losing the activity of tfdA during this step. The thus-produced plasmids pKJSB330, pKJS(X)630 and pKJS32RHΔS', described in Examples 4, 5 and 7, are capable of expressing tfda gene activity. In this way, the position of the gene can be delimited to an XbaI/SalI fragment of the size of 1.4 kilobases.

By the deletion, disclosed in Example 16, of variously long DNA segments from the double-stranded forms of the recombinant phages MJSS'030 and MJSS'031 by means of exonuclease III, a number of phages can be produced wherein respectively different regions of the cloned DNA lie closest to the starting point for sequencing. The sequence of a 2-kilobase BamHI/SalI fragment can then be composed of the partial regions sequenced in overlapping relationship. From a knowledge of the base sequence, further properties of the tfda-containing DNA can then be derived, such as, for example, the position and length of the encoding region and the position of restriction scission sites, which can be of considerable utility for the further use of tfdA.

By deletion of DNA fragments from tfda-containing plasmids and, respectively, by subcloning DNA fragments, it is also possible to obtain further plasmids according to this invention which then merely contain parts of a tfda gene. Thus, for example, by subcloning the 1.5-kilobase EcoRI/BamHI fragment from pKJS32 into pKT231, the plasmid pKJEΔB130 is obtained which merely contains the 5' end of tfda, i.e. the promoter and the sequence coding for the N-terminus, and which is no longer capable of expressing an enzymatically active gene product. Parts of genes can be utilized for the construction of plasmids wherein the 5' end of a coding DNA, including its promoter, are linked in the same reading raster with the 3' end of another coding DNA and thus lead to expression of a so-called fusion protein in those organisms recognizing the respective promoter.

Another possibility of modifying the plasmids of this invention resides in the insertion of a foreign DNA segment. The insertion can serve for the introduction of new functional DNA sequences, e.g. of restriction scission sites, promoters, resistance genes, translation and transcription stop signals. The insertion of a portion of a foreign gene sequence can also lead to the formation of fusion proteins.

One example of insertion of a foreign DNA is the insertion of the omega fragment into the BglII scission site of the plasmid pTJS'X535 located in the center of the coding region of tfdA (Example 11). With this fragment, translation stop codons are incorporated in all reading rasters and transcription stop signals are incorporated together with a selectable resistance to antibiotics. As can be confirmed by specific radio-active labeling of the gene product as well as by in vivo enzyme test for 2,4-D-monooxygenase (Example 15), this results in the expression of a shortened, no longer enzymatically active protein by the recombinant plasmid pTJS'X535omega.

Cloned fragments containing tfda or parts of tfdA can serve for the detection of homologous DNA sequences and thus for finding tfda genes in other organisms. For this purpose, these fragments are excised from the plasmids of this invention with the aid of suitable restriction enzymes, isolated, and labeled in accordance with methods known from the literature, for example by incorporation of radionuclides. By means of the conventional hybridization method, fragments can be identified in the entire DNA of an organism or in a gene bank produced therefrom, which fragments exhibit homology with tfda. In this way, it is possible to recognize even among a population of various organisms those which contain such a tfda-homologous sequence. The process can be utilized for tracking down novel 2,4-D-degrading organisms as well as for the discovery of tfdA genes in these organisms.

It is possible to transfer tfdA genes to other organisms either directly with the aid of the inventive plasmids insofar as they are suitable for this purpose, or after modification by means of conventional genetic engineering techniques. The transfer can pursue the objective of expressing the tfdA-coded 2,4-D-monooxygenase in these organisms and thus to imbue the latter with the property of being able to degrade 2,4-D or compounds similar to 2,4-D.

Thus it is possible, for example, by means of the conjugative transfer of tfda-containing plasmids with a wide host range into various gram-negative bacteria, described in Example 14, to impart to these bacteria the property of reacting 2,4-D or compounds similar to 2,4-D to the corresponding phenol. This, in conjunction with a degradation activity inherent in the respective strain, can lead to a broadening of the spectrum of compounds degradable by this strain. The strain Alcaligenes eutrophus JMP222 exhibits, for example, genes for metabolizing phenol. The expression of tfdA thus conveys to this strain the entirely novel possibility of utilizing phenoxyacetic acid as the growth substrate. The strain Pseudomonas B13 can metabolize phenol as well as 4-chlorophenol, and receives, by tfda, in an analogous fashion the capability of growing on phenoxyacetic acid and 4-chlorophenoxyacetic acid. Likewise possible is the degradation of variously substituted phenoxyacetic acids, such as 4-chloro-2-methylphenoxyacetic acid, 2,4,5-trichlorophenoxyacetic acid, and similar compounds, by organisms containing tfdA and capable of reacting the corresponding phenols. Even though the thereby attainable broadening of the spectrum of degradation activities of an organism will not in every case lead to the creation of a novel property heretofore not realized in nature, it can yet serve for qualitative improvement insofar as strains can thereby be constructed having a degrading power that is higher as compared with wild-type strains, or strains having higher tolerance against possibly toxic substrates or products of a degradation pathway. Such strains would prove useful specifically under conditions prevailing in artificial systems, rather than in a natural environment, such as, for example, in clarification systems for the purification of industrial wastewaters. An overview has recently been published regarding the yields attainable heretofore in the field of microbial degradation of halogenated aroamtic compounds with the aid of newly designed strains [D. Ghosal, I.-S. You, D. K. Chatterjee, A. M. Chakrabarty, 1985, Microbial Degradation of Halogenated Compounds; Science 228 : 135–142].

A further possibility of utilizing the gene tfdA resides in its transfer to plants. Methods for the transformation of plants with foreign DNA are known in the literature. Thus far, there are two primary methods which can be used for transferring exogenous genes to plants: One method uses the functions of the Ti plasmid from *Agrobacterium tumefaciens;*the other is based on the transformation of vegetable protoplasts with the aid of physical and chemical means and agents, such as "electroporation", thermal shock, treatment with calcium chloride or polyethylene glycol. While transformation of plant cells by either method is always possible, in principle, the regeneration of entire plants from individual cells or cell tissues is not achieved in every instance. At present, this represents the primary obstacle to the manipulation of monocotyledonous plants by genetic engineering.

A preferred objective of plant transformation with tfda is the expression of the gene characteristic, i.e. the 2,4-D-monooxygenase activity,in the transformed plant, thus enabling the plant to degrade the derivatives of phenoxyacetic acid, acting as an auxin-analogous plant hormone at low concentrations and as a growth inhibitor at high concentrations, to the phytochemically ineffective phenols. Accordingly, this property would have significance as a selectable marker for genetically transformed plants.

In order for a prokaryotic gene, such as tfdA, to be expressed in plant cells, it must be coupled with the plant-specific signal sequences necessary for transcription and translation. See Example 17. It has been mentioned that this coupling can take place by the coincidence-controlled integration of a gene into the genome of a plant transformed therewith. Prokaryotic genes, however, are combined with preference in vitro with the suitable plant-specific expression signals. A generally applicable method resides, for example, in linking the 5' end of a structural gene including the associated plant promoter with the coding sequence of the prokaryotic.gene in such a way that a fusion protein is synthesized in a plant cell transformed therewith. This fusion protein consists of the N-terminal amino acids of the plant protein and a predominant proportion of the prokaryotic protein and, in its essential properties, corresponds to the prokaryotic protein [R. T. Fraley et al., 1983, Expression of Bacterial Genes in Plant Cells, Proc. Natl. Acad. Sci. USA 80 : 4803; J. Paszkowski and M. W. Saul, 1986, Direct Gene Transfer to Plants, in S. P. Colowick and N. A. Kaplan (ed.), Methods in Enzymology 118 : 668]: A similar method utilizes solely the plant promoter, including a portion of the 5'-untranslated region of the transcribed m-RNA and makes do without the 5' end of the coding region of a plant gene. In the expression in plants, an ATG codon of the prokaryotic gene segment then serves as starting point for the translation. Analogously, the expression signals of plant viruses can be employed [N. Brisson and T. Hohn, 1986, Plant Virus Vectors; Cauliflower Mosaic Virus, in S. P. Colowick and N. O. Kaplan (ed.), Methods in Enzymology, 118 : 659]. Vectors for the expression of prokaryotic genes in plants are known in the literature and are generally available.

A prerequisite for construction of a gene expressible in plants from a prokaryotic gene with the aid of the aforementioned vector plasmids resides in knowing the base sequence as present for the gene tfda. Such knowledge permits exact localization of restriction cutting sites and thus makes it possible to link the various DNA segments in a base-accurate fashion. Furthermore, only such knowledge makes it feasible to perform controlled mutagenesis for the creation of novel, functionally significant DNA sequences, such as, for example, the. introduction of novel restriction cutting sites.

Using this information, a plant/bacterial hybrid gene for 2,4-dichlorophenoxyacetic acid monooxygenase (DPAM) can be constructed and inserted into various plasmids in order to effect transfer and expression of the gene in plants. The flanking sequences to the bacterial gene, both 5' and 3', may be engineered by means known in the art for making the hybrid gene capable of expression in the plant. For example, constitutive or inducible promoters may be inserted at the 5'-end of the gene. In addition, 3'-signal sequences, such as, for example, termination and/or polyadenylation sequences, may be inserted in the plasmid to improve expression of the cloned gene.

The recombinant plasmid may then be transferred to plants by known methods; for example, either directly using vegetable protoplasts or via the Ti plasmid from *Agrobacterium tumefaciens* as described above. Other intervening steps known for tailoring plasmids for particular uses may be incorporated as well. If the Ti plasmid method is used, for example, intermediate plasmids may be constructed to allow expression of DPAM in a bacterial species, such as, for example, *E. coli*, which can carry and mobilize cointegrates of cloning vectors and disarmed Ti plasmids. Agrobacterium strains carrying the new plasmids are then used to infect plant cells.

Transgenic plants constructed according to these procedures can be grown in the presence of concentrations of certain substituted phenoxyacetic acids which are normally growth-inhibiting for untransformed plants. For example, tissue cultures of tobacco plants (*Nicotiana tabacum* W38) transformed with the DPAM gene of this invention under the control of a constitutive promoter from cauliflower mosaic virus demonstrate up to a 20-fold higher tolerance for 2,4-D than their untransformed counterparts (see Example 20) and transgenic plants grown in soil show at least a 10-fold higher tolerance.

This invention also includes the provision of antibodies, especially monoclonal antibodies, anti:1 body fragments, for example, Fab fragments, and labelled antibodies which are capable of binding 2,4-D-monooxygenase, and which are prepared according to fully conventional techniques.

The invention will be explained in greater detail below with reference to illustrations and examples. In the examples, methods of genetic engineering have been utilized as they are generally known and well-tested in this field of art. Cloning of genes and analysis of gene structures were performed according to standard methods of genetic engineering as they have already been incorporated into the textbooks by E.-L. Winnacker ("Gene und Klone" [Genes and Clones], Chemie Publishers, Weinheim, 1985) and by R. W. Old and S. B. Primrose (Principles of Gene Manipulation, Blackwell Scientific Publ., Oxford, 1985). The methods and techniques have in each case been updated to the most recent status e.g. in I. K. Setlow and A. Hollaender (Genetic Engineering: Principles and Methods, Plenum Publ. Corp., N.Y.). Besides the specific publications, general working directions in the form of laboratory manuals have also been utilized in many instances [R. W. Davis et al., Advanced Bacterial Genetics: a Manual for Genetic Engineering; T. Maniatis et al., Molecular Cloning; T. J. Silhavy et al., Experiments with Gene Fusions, all from Cold Spring Harbor Lab.,N.Y.; A. Pühler and K. N. Timmis, Advanced Molecular Genetics, Springer, Berlin, 1984; D. M. Glover, DNA Cloning: a Practical Approach, JRL Press, Oxford, Washington, D.C., 1985].

On Aug. 28, 1986, the following microorganisms were deposited with the Deutsche Sammlung von Mikroorganismen [German Collection of Microorganisms] (DSM) in Göttingen, Federal Republic of Germany (deposit number):

| | |
|---|---|
| E. coli HMS 174 (pT7-5) | (DSM 3829) |
| E. coli HMS 174 (pT7-6) | (DSM 3830) |
| E. coli JA 221 (pGSS33) | (DSM 3831) |
| E. coli LE 392 (pTJSS'035) | (DSM 3832) |
| E. coli HB101 (pVK101) | (DSM 3833) |
| E. coli SK1592 (pKT231) | (DSM 3834) |
| E. coli S17-1 (pKJS31) | (DSM 3835) |

-continued

| | |
|---|---|
| E. coli S17-1 (pKJS32RHΔS') | (DSM 3836) |
| E. coli S17-1 (pKJS(X)630) | (DSM 3837) |
| E. coli SBC107 (pRME1) | (DSM 3838) |
| E. coli K38 (pGT1-2/pTJS'X535) | (DSM 3839) |
| Alcaligenes eutrophus JMP134 (pJP4) | (DSM 3840) |
| Alcaligenes eutrophus JMP222 | (DSM 3841) |
| Alcaligenes eutrophus JMP134:Tn5-2 (pJP4:Tn5-2) | (DSM 3842) |
| Alcaligenes eutrophus JMP134:Tn5-4 (pJP4:Tn5-4) | (DSM 3843) |

DETAILED DESCRIPTION OF THE DRAWINGS

Abbreviations:

Ap—ampicillin resistance

Km—kanamycin resistance kb—kilobases

M—molecular weight marker kD—kilodalton

Figure 1:
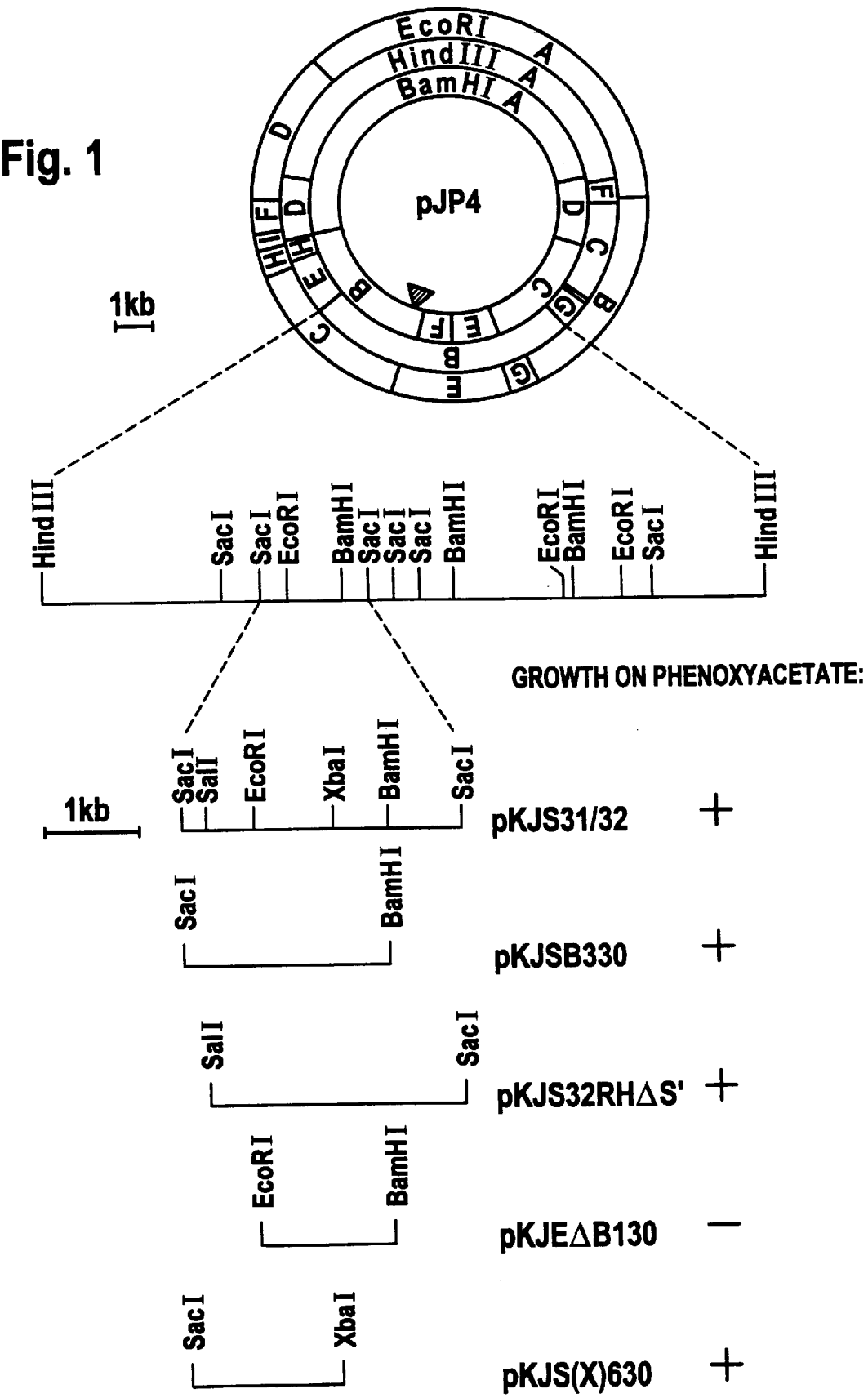

FIG. 1—shows origin and restriction map of the HindIII fragment cloned from pJP4, having a size of 21 kb (Example 1) and of the thus-derived subfragments (Examples 3–7), as well as the expression of phenoxyacetic acid degradation in Alcaligenes eutrophus JMP222 by the corresponding plasmids with a wide host range (Example 14). The arrow marks the exact location of tfda in the plasmid pJP4.

Figure 2:
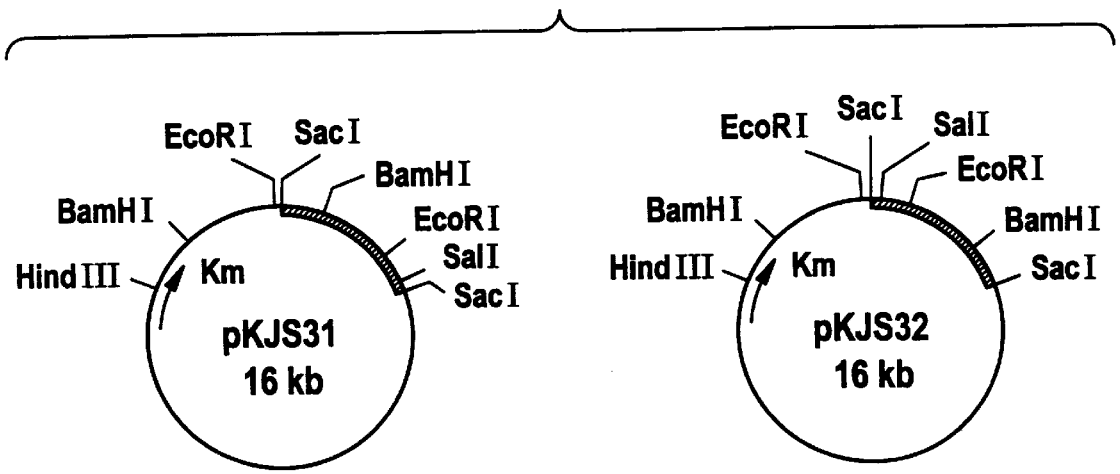
Figure 3:
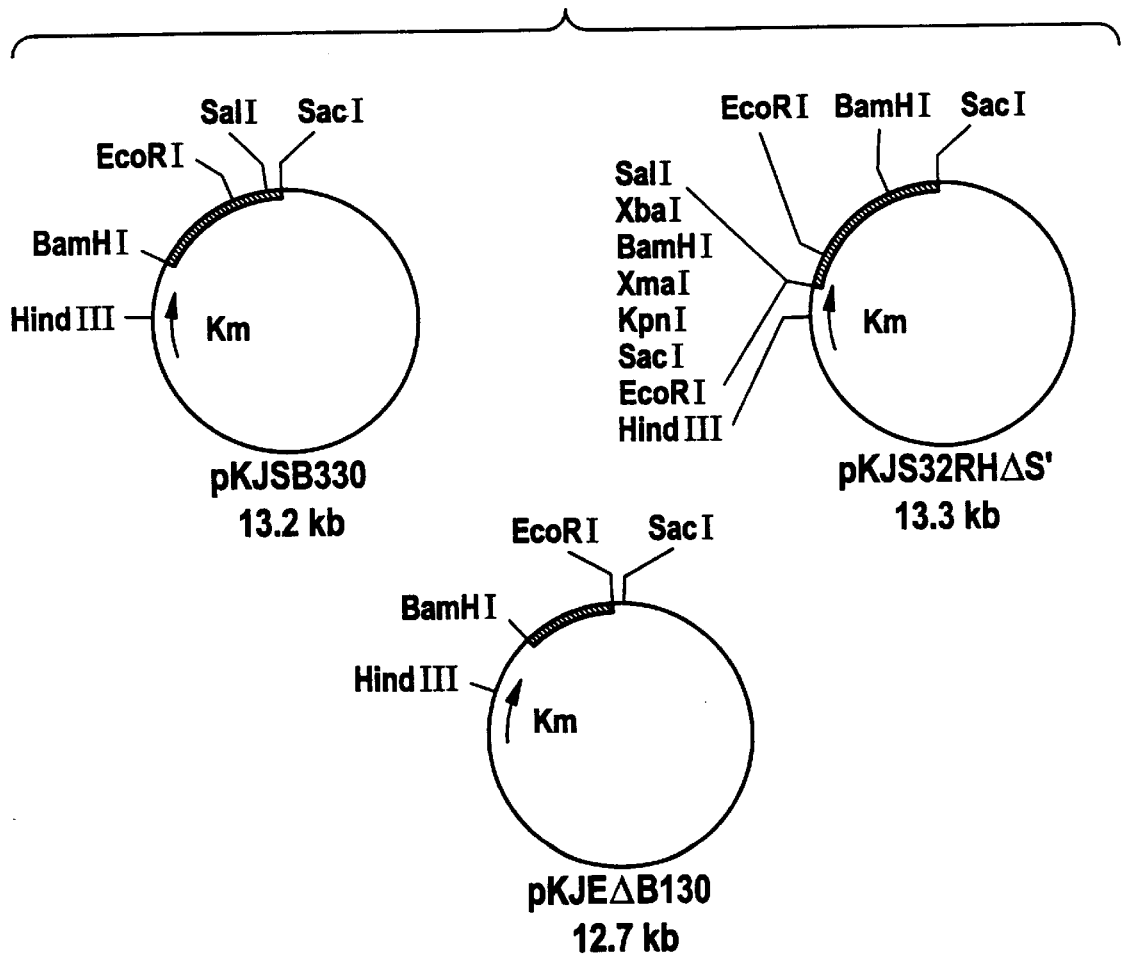
Figure 4:
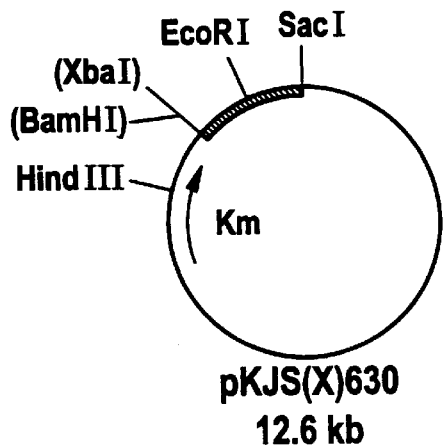

FIGS. 2, 3, 4- show the plasmids derived from pKT231 containing tfda or parts of tfda (Examples 3–7). The thin lines denote the proportion stemming from the vector plasmid; the fat lines denote the insert stemming from pJP4.

Figure 5:
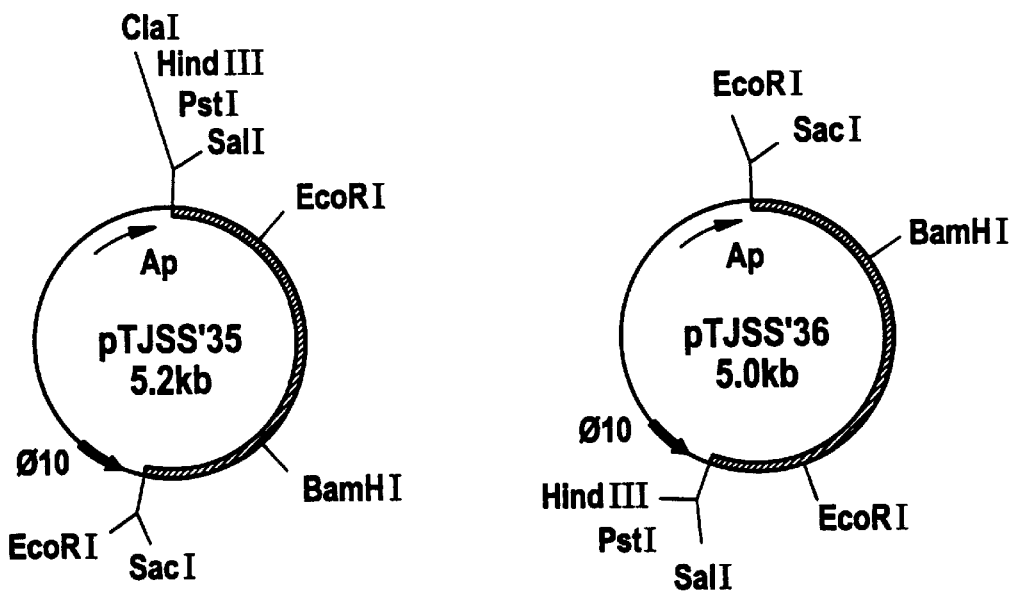

FIGS. 5, 6, 7a—show the plasmids derived from the T7 promoter plasmids pT7-5 and pT7-6 with tfdA-containing insert fragments (Examples 8–11). The thin lines denote the proportion stemming from the vector plasmid; the fat lines denote the insert stemming from pJP4.

Figure 7B:
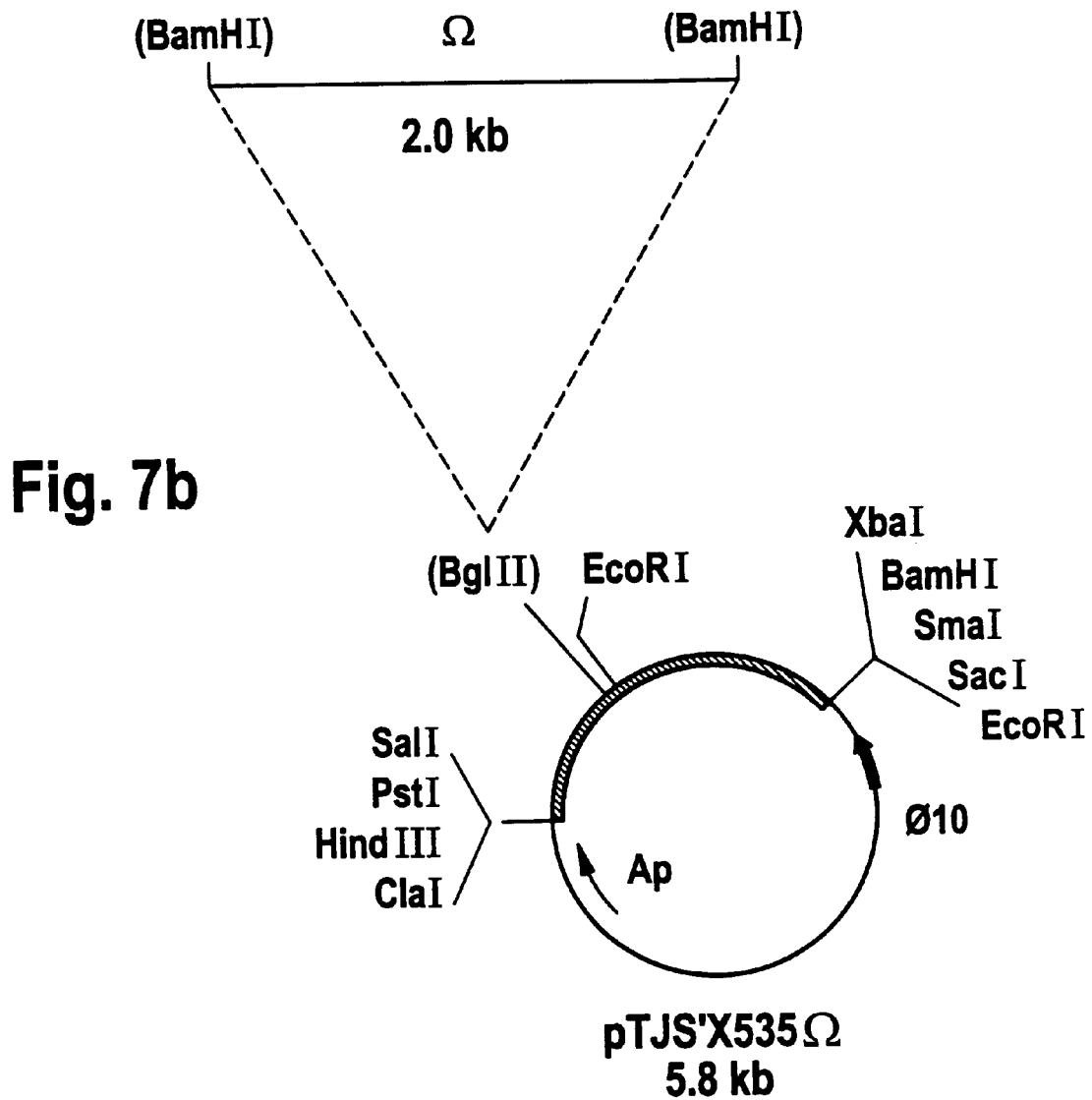

FIG. 7b—shows the insertion of the omega fragment in the plasmid pTJS'X535 (Example 11).

Figure 8:
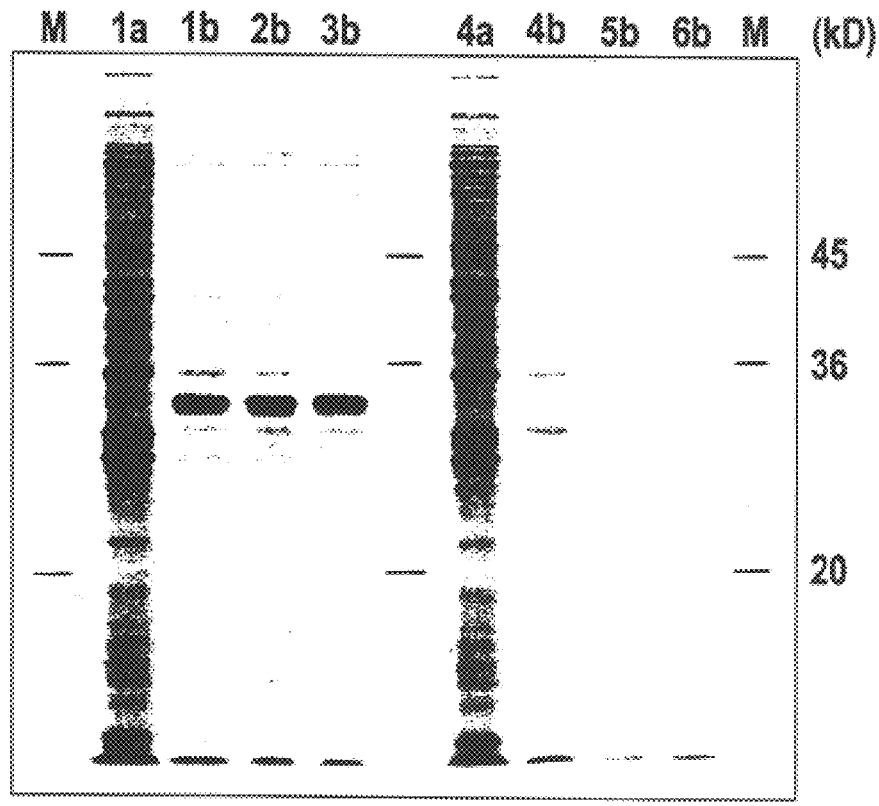

FIG. 8—shows specifically radiolabeled proteins on the autoradiogram of a polyacrylamide gel, which proteins are expressed in high yield by the tfda-containing plasmids with the aid of the T7 promoter (Example 15).

1: pTJSS'035; 2: pTJS'B435; 3: pTJS'X535;

4: pTJSS'036; 5: pTJS'B436; 6: pTJS'X536.

a denotes completely marked total cell protein, b denotes protein specifically marked after induction of the T7 promoter.

Figure 9:
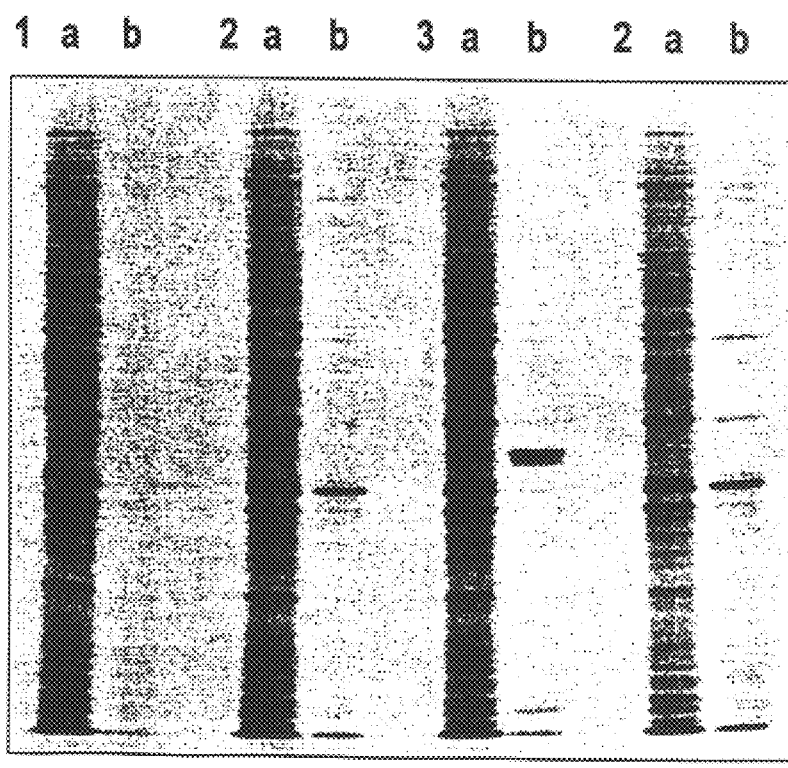

FIG. 9—shows the shortened tfda gene product expressed by plasmid pTJS'X535 omega with the aid of the T7 promoter (2b), as compared with the unshortened protein expressed by pTJS'X535 (3b) and with the insert-free vector plasmid pT7-5 (1b).

FIG. 10—shows the base sequence of the BamHI/SalI fragment having a length of 2058 bases, on which the gene tfdA is transcribed from the 5' end toward the 3' end. The arrows designate the beginning and end of the coding region of tfdA (Example 16).

Figure 11:
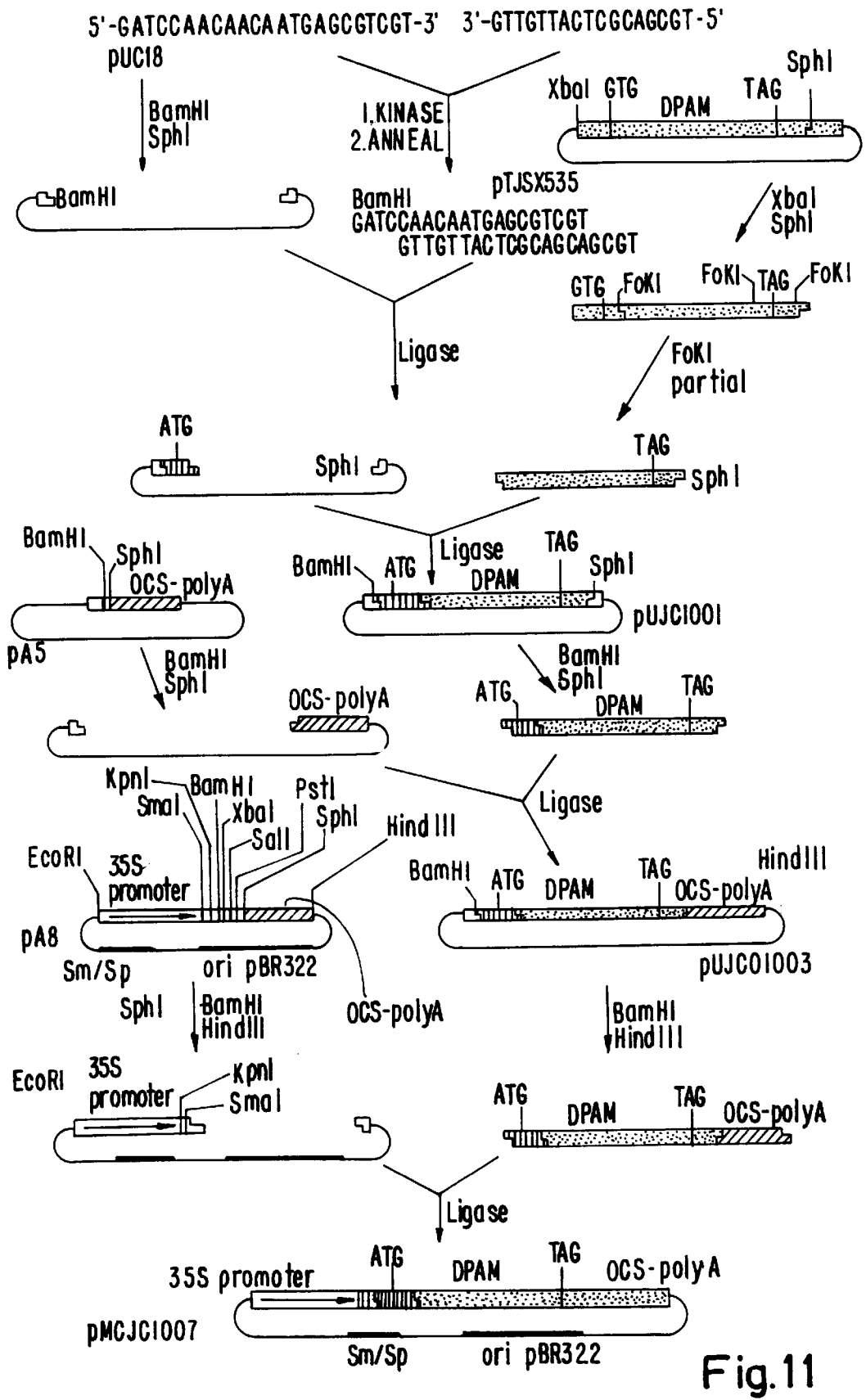

FIG. 11 Construction of plasmid pMCJC1007 for stable integration and expression of the DPAM gene in plants. In a first cloning step the procaryotic translation start codon GTG of gene tfda was replaced by a synthetic oligonucleotide. To avoid dimerization at the BamHI site the oligonucleotide was linked in a two step ligation first to the BamHI end of linearized pUC18 and then to the DPAM coding sequence. In two following cloning steps the BamHI- SphI fragment containing the hybrid construct was inserted into the plant expression vector plasmid pA8, between the CaMV 35S promoter and the OCS 3' end. As pA8 contains a second SphI site outside of its polylinker, pA5 was used to form an intermediate plasmid based on pUC18.

FIG. 12 Tolerance of transgenic tobacco against 2,4-D in tissue culture. Explants from Nicotiana tabacum W38 control plants (left) and transgenic plants (right) were incubated on medium containing 1.0 mg/l 2,4-D. Normal shoots develop from leaf discs which constitutively express DPAM (A, right). Transgenic explants with a light-inducible DPAM gene (B, right) show the same sensitivity against 2,4-D as the nontransformed tobacco W38 (left).

Figure 13:
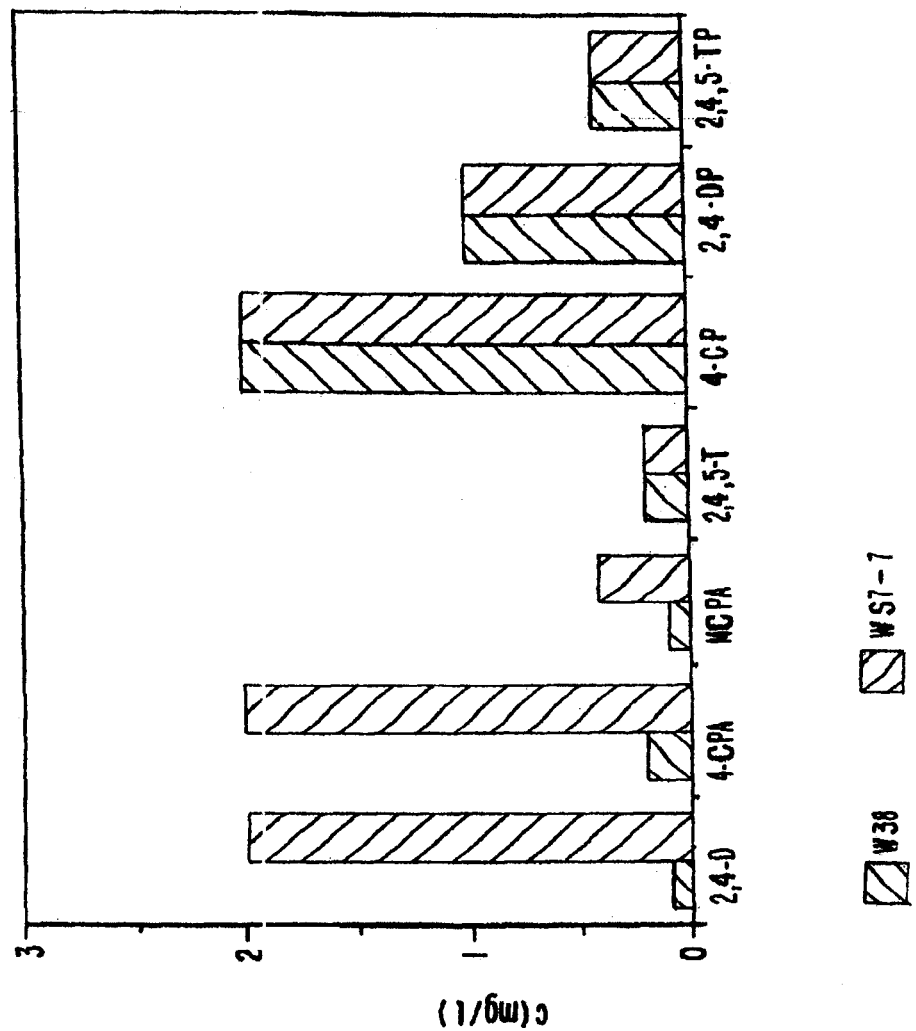

FIG. 13 Cross tolerance of transgenic tobacco against other phenoxy herbicides. Substances listed below were incorporated into 2MS agar as described in the text. The graphic demonstrates the response of control tobacco (W38) and transgenic tobacco (WS7-7) against different synthetic auxins. The height of the bars indicates the concentration limit up to which cells from explanted leaf discs could differentiate into normal shoots. At higher concentration only callus growth was possible. 2,4-D: 2,4-dichlorophenoxyacetic acid, 4-CPA: 4-chlorophenoxyacetic acid, MCPA: 4-chloro-2-methylphenoxyacetic acid, 2,4,5-T: 2,4,5-trichlorophenoxyacetic acid, 4-CP: 2-(4-chlorophenoxy)propionic acid, 2,4-DP: 2-(2,4-dichlorophenoxy)propionic acid, 2,4,5-TP: 2-(2,4,5-trichlorophenoxy)propionic acid.

Figure 14A:
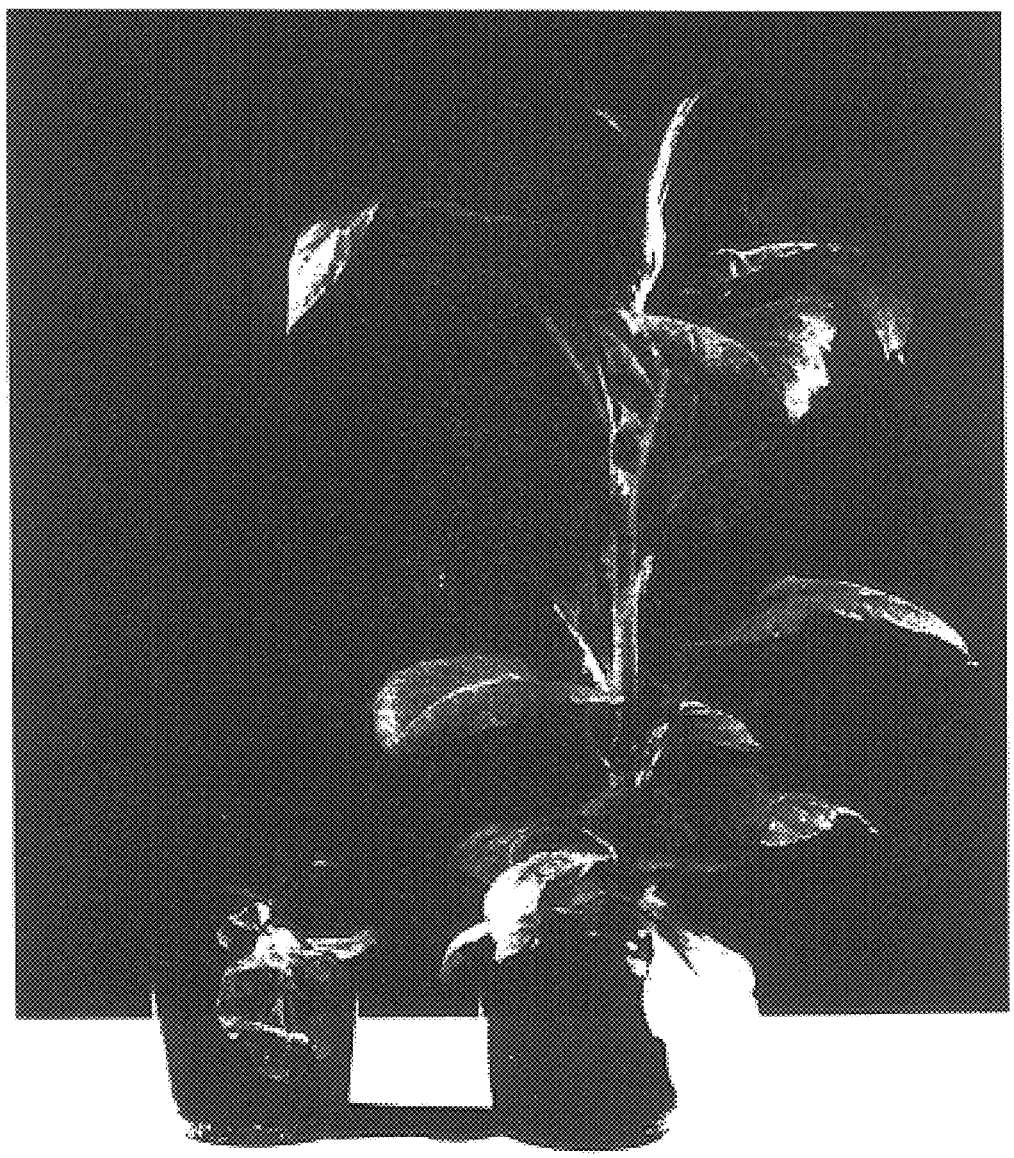
Figure 14B:
Figure 11:
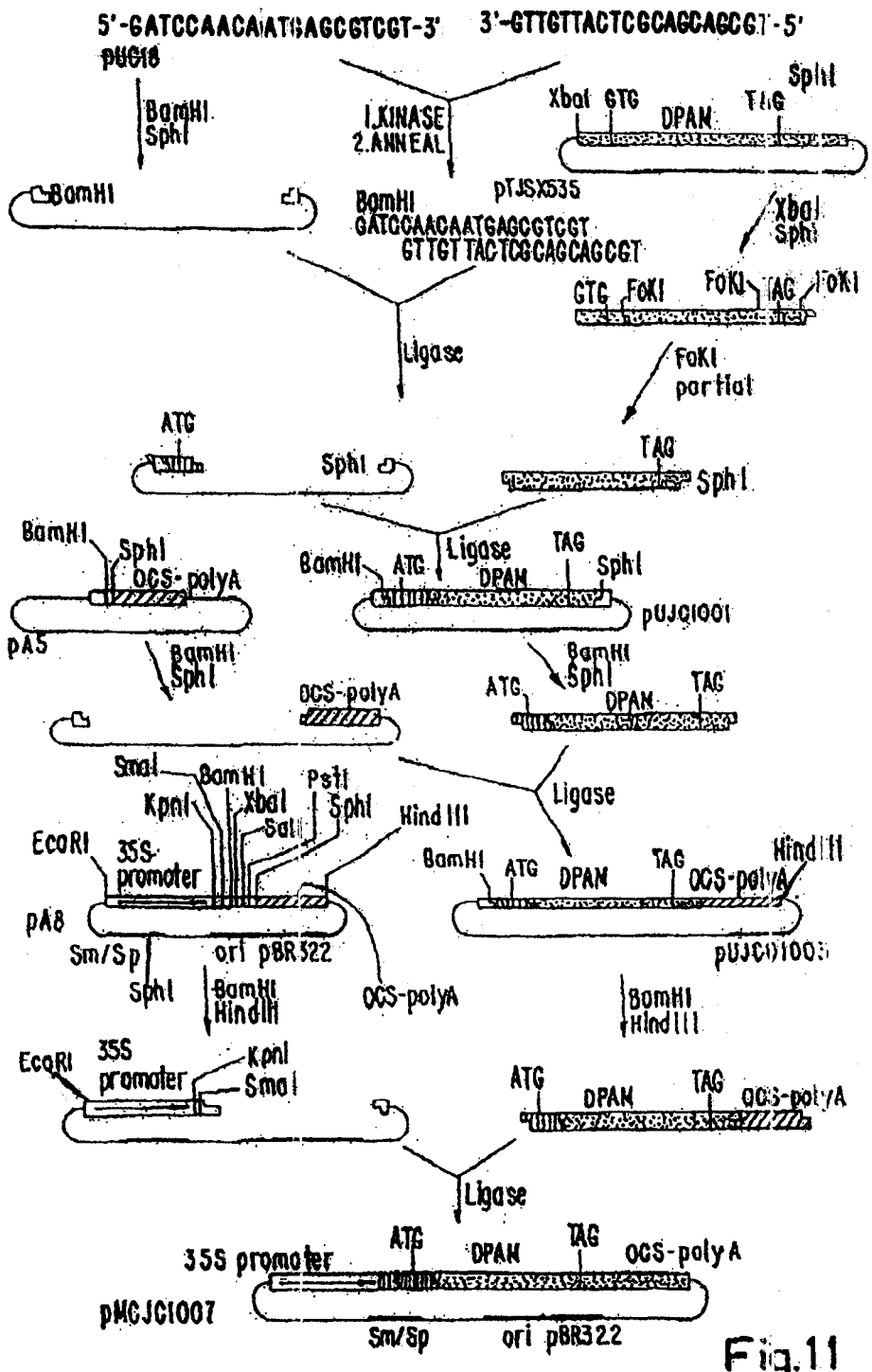

FIGS. 14A and 14B Effect of 2,4-D on transgenic tobacco plants. A, left: a Nicotiana tabacum W38 control plant; the plant on the right is a clonal replicate of the WS7—7 line, which expresses the DPAM gene under the control of the CaMV 35S promoter. Both plants were sprayed with 10 kg/ha 2,4-D-Na. B, left: a Nicotiana tabacum W38 control plant; the plant on the right is a clonal replicate of the WS4–7 line, which expresses the DPAM gene under the control of the light-inducible ST-LS1 promoter. Both plants were sprayed with 1 kg/ha 2,4-D-Na.

EXAMPLE 1

Preparation of Plasmid pVJH21

(a) Isolation of Plasmids pJP4 and pVK101

Alcaligenes eutrophus JMP134 is incubated in 250 ml of PYF medium (peptone, 3 g/l; yeast extract, 3 g/l; fructose, 2 g/l) for 16 hours at 30° C. The plasmid pJP4 is isolated from the centrifuged cells in accordance with the procedure from J. Bacteriol. 135 : 227 (1978). The plasmid pVK101 [V. C. Knauf et al., Plasmid 8 : 45 (1982)] is isolated from E. coli HB101 according to the generally known process of alkaline lysis by T. Maniatis et al. (Molecular Cloning: a Laboratory Manual, Cold Spring Harbor Laboratory, Cold Spring Harbor, New York, 1982)

(b) Cloning of the 21-kilobase HindIII Fragment from pJP4

A reaction mixture consisting of 20 μl (500 ng) of pJP4, 2.5 μl of TAS buffer (0.33 M trisacetate, 0.65 M potassium acetate, 0.1 M magnesium acetate, 5 mM dithiothreitol (DTT), 30 mM spermidine, pH 7.9) and 2.5 μl (1 unit) of a diluted HindIII solution is incubated at 37° C. for 120 minutes. A further reaction mixture consisting of 50 μl (14 μg) of pVK101, 5.5 μl of TAS buffer and 1 μl (20 units) of undiluted HindIII solution is incubated at 37° C. for 90 minutes. Then 1 μl (30 units) of calf intestinal alkaline phosphatase (DIP, Boehringer, Mannheim) is added and the mixture is incubated for another 60 minutes. Respectively 9 μl of each of the two reaction mixtures is separated on a 0.7% low-melting agarose gel by electrophoresis. The gel is subsequently stained for 15 minutes in an ethidium bromide solution (5 μg/ml) and the DNA bands are made visible in UV 300 nm. The individual 20 kb band of pVK101 restriction, as well as the second-largest band (21 kb) of pJP4 restriction are excised from the gel, both bands are combined, and the DNA is isolated from the agarose according to the procedure by T. Maniatis et al. (Molecular Cloning: a Laboratory Manual, Cold Spring Harbor Laboratory, Cold Spring Harbor, N.Y., 1982). The ethanol-precipitated DNA is taken up in 10 μl of ligation buffer (66 mM Tris-HCl, 6.6 mM MgCl$_2$, 10 mM DTT, 1 mM ATP, pH 7.5), combined with 1 μl (0.1 unit) of diluted T4-DNA ligase, and incubated for 16 hours at 14° C. (=ligation batch). Competent cells of E. coli S17-1 [Biotechnology 1 : 784 (1983)] are produced according to the method by T. J. Silhavy et al. (Experiments with Gene Fusions, Cold Spring Harbor Laboratory, Cold Spring Harbor, N.Y., 1984), and 0.2 ml of the thus-obtaiend competent cells are mixed with 5 μl of ligation batch, left for 40 minutes on ice, then heated for 3 minutes to 42° C. (=transformation), subsequently diluted with 2 ml of LB medium according to T. Maniatis et al. (cf, above), and incubated for 60 minutes at 30° C. (=phenotypic expression). Then portions of respectively 0.2 ml are spread out on LB agar plates containing 10 pl/ml of tetracycline. The plates are cultured at 37° C. for 16 hours. Several tetracycline-resistant colonies are found.

(c) Identification of pVJH2

In accordance with the process of alkaline lysis, an instant preparation of the plasmid DNA is performed on the thus-obtained tetracycline-resistant colonies, as described by T. Maniatis et al. The aforedescribed process of treatment with alkaline phosphatase ensures that each of the tetracycline-resistant clones contains the desired insert. The recombinant plasmids are identified by restriction enzyme digestion with EcoRI and subsequent electrophoretic separation of the DNA fragments in a 0.7% agarose gel according to T. Maniatis et al. (compare above). By comparing the sizes of the thus-obtained EcoRI fragments with the size relationships known from the literature with respect to EcoRI and HindIII for pJP4 and pVK101 [R. H. Don, J. Bacteriol. 161 : 466 (1985) and V. C. Knauf et al., Plasmid 8 : 45 (1982)], an exact identification is provided of the insert DNA as well as of its orientation in the vector plasmid pVK101.

(d) Restriction Map of the HindIII Insert in pVJH21

A thus-obtained strain containing the plasmid pVJH21 is incubated in 400 ml of LB medium containing 20 μg/ml of tetracycline for 16 hours at 37° C. From the centrifuged cells, the plasmid DNA is isolated according to the method of alkaline lysis by T. Maniatis et al. (see above). The isolated plasmid DNA of pVJH21 is digested in various batches with the enzymes EcoRI, BamHI and SacI individually, as well as with the following nine combinations of several enzymes: EcoRI/BamHI (1); EcoRI/SacI (2); BamHI/SacI (3); HindIII/EcoRI (4); HindIII/BamHI (5); HindIII/SacI (6); HindIII/EcoRI/BamHI (7); HindIII/EcoRI/SacI (8); and HindIII/BamHI/SacI (9). The DNA fragments are separated in a 0.7% agarose gel according to T. Maniatis et al. (see above), and their sizes are determined by comparison with HindIII-cut lambda-DNA. The restriction map is drawn with the thus-obtained data together with the size relationships known for the plasmids pJP4 [R. H. Don, J. Bacteriol. 161 : 466 (1985)] and pVK101 [V. C. Knauf et al.,Plasmid 8 : 45 (1982)] with respect to EcoRI, BamHI and HindIII.

EXAMPLE 2

Production of Plasmid pGJS3

(a) Isolation of Plasmids pVJH21 and pGSS33

The recombinant strain *E. coli* S17-1 containing the plasmid pVJH21 prepared in Example 1, and *E. coli* JA221 with the vector plasmid pGSS33 [G. S. Sharpe, Gene 29 : 93 (1984)] are incubated in respectively 300 ml of LB medium containing 20 μg/ml of tetracycline for 16 hours at 37° C. The two plasmids are isolated from the centrifuged cells in accordance with the method of alkaline lysis by T. Maniatis et al. (see above).

(b) Cloning of SacI Fragments from pVJH21

A reaction mixture consisting of 10 μl (5 μg) of pVJH21, 10 μl (1 μg) of pGSS33, 4 μl of TAS buffer, 16 μl of water, and 0.5 μl (10 units) of SacI is incubated at 37° C. for 90 minutes. The restriction enzyme is subsequently inactivated by heating to 68° C. for 15 minutes. The DNA is precipitated with ethanol according to T. Maniatis et al. (see above), and the dried precipitate is taken up in 40 μl of ligation buffer. After addition of 1 μl (1 unit) of T4-DNA ligase, the ligation batch is incubated for 16 hours at 14° C. *E. coli* LE392 [N. E. Murray et al., Mol. Gen. Genet. 150 : 53 (1977)] is rendered competent for DNA reception according to the method by T. J. Silhavy et al. (Experiments with Gene Fusions, Cold Spring Harbor Laboratory, Cold Spring Harbor, N.Y., 1984); 0.2 ml of competent cells is combined with 5 μl of ligation batch, left on ice for 40 mintues, and transformed by 3 minutes of heating to 42° C. After dilution with 2 ml of LB medium and incubation at 30° C., portions of 50 μl to 200 μl are spread on LB agar plates containing 20 μg/ml of chloramphenicol. The plates are incubated for 16 hours at 37° C.

(c) Identification of Recombinant Plasmids

The thus-obtained chloramphenicol-resistant clones are spread parallel on two LB agar plates, one of which contains 25 μg/ml of streptomycin, the other of which contains 20 μg/ml of chloramphenicol. The plasmid DNA is isolated from clones that prove streptomycin-sensitive in this test with the aid of the instant method of alkaline lysis according to T. Maniatis et al. (see above). The size of the inserts contained in vector pVK101 is determined by restriction of the isolated plasmids with SacI, electrophoretic separation of the DNA fragments on a 0.7% agarose gel, and comparison of the bands visible in UV 300 nm with known fragments of a HindIII restriction of lambda phage DNA. The plasmid pGJS3 is a recombinant plasmid from pGSS33 and a DNA fragment having a size of 3 kilobases. Since the plasmid pVK101 per se has no scission site for SacI, the cloned DNA fragment clearly stems from the HindIII fragment, having a size of 21 kilobases, of pJP4.

EXAMPLE 3

Preparation of Plasmids pKJS31 and pKJS32

(a) Isolation of Plasmids pGJS3 and pKT231

The strain *E. coli* LE392 produced in Example 2, containing the recombinant plasmid pGJS3, is cultured in 400 ml of LB medium with an addition of 20 μg/ml of chloramphenicol for 16 hours at 37° C. *E. coli* SK1592 with the vector plasmid pKT231 [M. Bagdasarian et al., Current Topics in Microbiology and Immunology, 96 : 47 (1982)] is incubated in 400 ml of LB medium with an addition of 50 μg/ml of kanamycin under the same conditions. The two plasmids are isolated from the centrifuged cells according to the process of alkaline lysis by T. Maniatis et al. (see above).

(b) Transcloning of the SacI Fragment from pGJS3 into pKT231

A reaction mixture consisting of 40 μl (400 ng) of pGJS3, 4 μl (100 ng) of pKT231, 6 μl of TAS buffer, 9 μl of water, and 1 μl (1 unit) of dilute SacI solution is incubated at 37° C. for 120 minutes. The restriction enzymes are inactivated by subsequent heating of the reaction mixture to 68° C. for 15 minutes. The batch is combined with 39 μl of water, 10 μl of 10-fold concentrated ligation buffer, and 1 μl (0.1 unit) of a dilute T4-DNA ligase, and the ligation batch is incubated for 16 hours at 14° C. An amount of 0.2 ml of competent cells of *E. coli* LE392, prepared according to the process by T. J. Silhavy et al. (Experiments with Gene Fusion, Cold Spring Harbor Laboratory, Cold Spring Harbor, N.Y., 1984) is mixed with 10 μl of the ligation batch, left on ice for 40 minutes, heated for 3 minutes to 42° C., mixed with 2 ml of LB medium, and incubated at 37° C. for 60 minutes. Portions of 50 μl to 200 μl are spread on LB agar plates containing 50 μg/ml of kanamycin. The plates are incubated at 37° C. for 16 hours.

(c) Identification of Recombinant Plasmids

The thus-obtained kanamycin-resistant clones are spread in parallel on three different LB agar plates, one of which contains 25 μg/ml of streptomycin, the second containing 20 μg/ml of chloramphenicol, and the third plate containing 50 μg/ml of kanamycin. Clones that turn out in this test to be sensitive to streptomycin and chloramphenicol, but resistant to kanamycin contain, in the normal case, a recombinant plasmid from the vector pKT231 (kanamycin resistance) and from the 3-kilobase SacI fragment from pGJS3. The size of the inserted DNA is determined by isolating the plasmid DNA according to the conventional instant method by T. Maniatis et al. (see above), restriction of the DNA with SacI and subsequent analysis of the fragments by electrophoresis in a 0.7% agarose gel. Plasmids having differing orientation of the insert in relation to the vector plasmid are identified by a restriction analysis with EcoRI carried out in the same way. The plasmid pKJS32 constitutes that form of the two possibilities wherein the EcoRI site of the insert is located closest to the EcoRI site of the vector proportion. This plasmid yields two EcoRI fragments of a size of 0.9 and 15 kilobases. The plasmid pKJS31 represents the construction with the opposite orientation of the insert, yielding two EcoRI fragments of the sizes 2.3 and 13.5 kilobases.

EXAMPLE 4

Production of Plasmid pKJSB330

(a) Isolation of Plasmid pKJS31

The clone of *E. coli* LE392 obtained in Example 3 and containing the recombined plasmid pKJS31 is incubated in 400 ml of LB medium with an addition of 50 μg/ml of kanamycin at 37° C. for 16 hours, and from the centrifuged cells the plasmid DNA is isolated by means of alkaline lysis according to T. maniatis et al. (see above).

(b) Deletion of Smaller BamHI Fragment from pKJS31

A reaction mixture consisting of 10 μl (500 ng) of pKJS31, 7 μl of water, 2 μl of TAS buffer and 1 μl (1 unit) of a diluted BamHI solution is incubated for 60 minutes at 37° C., and subsequently the enzymatic reaction is stopped by heating to 68° C. for 15 minutes. The restriction batch is then combined with 50 μl of water, 8 μl of 10-fold concentrated ligation buffer, and 2 μl (2 units) of T4-DNA ligase and incubated for 16 hours at 14° C. A mixture is prepared from 0.2 ml of competent cells of *E. coli* S17-1, produced according to the conventional method by T. J. Silhavy et al.

(Experiments with Gene Fusions, Cold Spring Harbor Laboratory, Cold Spring Harbor, N.Y., 1984), and 10 μl of the ligation batch, left on ice for 40 minutes, heated to 42° C. for 3 minutes, mixed with 2 ml of LB medium, and incubated for 60 minutes at 37° C. Portions of 50 μl to 200 μl are spread on LB agar plates containing 50 μg/ml of kanamycin. The plates are incubated for 16 hours at 37° C.

(c) Identification of the Shortened Plasmids

The plasmid DNA is isolated from the thus-obtained kanamycin-resistant clones by means of the known instant method of alkaline lysis by T. Maniatis et al. (see above). By restriction of the plasmids with BglII and and electrophoretic separation of the DNA fragments in a 0.7% agarose gel, plasmids are identified which have lost the small BamHI fragment from pKJS31. These plasmids possess only a single BglII scission site and therefore yield a BglII fragment having a size of 13.2 kilobases. They can thus be clearly differentiated from their origin plasmid pKJS31 and are denoted as pKJSB330.

EXAMPLE 5

Production of Plasmid pKJS32RHΔS'

(a) Isolation of Plasmids pKJS32 and pRMEl

The clone of E. coli LE392 obtained in Example 3 and containing the recombined plasmid pKJS32, as well as E. coli SBC107 (pRMEl) are cultured in respectively 400 ml of LB medium with an addition of 50 μg/ml of kanamycin at 37° C. for 16 hours. The plasmids are isolated from the centrifuged cells by alkaline lysis according to T. Maniatis et al. (see above).

(b) Deletion of a HindIII/SalI Fragment from pKJS32 and Subsequent Insertion of a HindIII/SalI Fragment from pRMEl A reaction mixture consisting of 10 μl (500 ng) of pKJS32, 10 μl (1 μg) of pRMEl, 15 μl of water, 4 μl of TAS buffer, 0.5 μl (1 unit) of dilute HindIII solution, and 0.5 μl (1 unit) of dilute SalI solution is incubated for 120 minutes at 37° C., and the enzymatic reaction is stopped by heating to 68° C. for 15 minutes. Then 10 μl of the restriction batch is combined with 25 μl of water, 4 μl of 10-fold concentrated ligation buffer and 1 μl (1 unit) of T4-DNA ligase and the mixture is incubated for 16 horus at 14° C. Cells of E. coli S17-1 rendered competent according to a conventional process by T. J. Silhavy et al. (Experiments with Gene Fusions, Cold Spring Harbor Laboratory, Cold Spring Harbor, N.Y., 1984). are mixed with 10 μl of the ligation batch, left on ice for 40 minutes, heated for 3 minutes to 42° C., and, after mixing with 2 ml of LB medium, incubated at 37° for 60 minutes. Portions of 5 μl to 200 μl are spread on LB agar plates containing 50 μg/ml of kanamycin. The plates are incubated for 16 hours at 37° C.

(c) Identification of the Recombinant Plasmids

The plasmid DNA is isolated from the thus-produced kanamycin-resistant clones by the conventional instant method of alkaline lysis according to T. Maniatis et al. (see above). By restriction with BamHI and electrophoretic separation of the resultant DNA fragments, plasmids are identified wherein, starting from pKJS32, the smaller DNA segment between the HindIII cutting site located on the vector portion in the middle of the kanamycin resistance gene and the SalI cutting site located on the insert has been removed and replaced by that HindIII/SalI fragment from pRMEl carrying the 3' end of the coding region of the kanamycin resistance gene. These plasmids yield two BamHI fragments having the lengths of 13.3 and 2.0 kilobases and thus clearly differ from the starting products and other possible byproducts of the ligation. They represent structures wherein a 0.2-kilobase DNA segment of the 3.0-kilobase insert of pKJS32 has been removed and wherein a part of the kanamycin resistance gene has been exchanged against another gene fragment of the same genetic origin. These plasmids are called pKJS32RHAS'.

EXAMPLE 6

Preparation of Plasmid pKJEΔB130

(a) Isolation of Plasmids pKT231 and pKJS32

The isolation of pKT231 was described in Example 3, that of pKJS32 in Example 5.

(b) Cloning of the Smaller EcoRI/BamHI Fragment from pKJS32 in pKT231

Two reaction mixtures, one consisting of 10 μl (500 ng) of pKJS32, 5 μl of water, 2 μl of TAS buffer, and respectively 1 μl (1 unit) of dilute solutions of the enzymes EcoRI, BamHI and PstI, the other consisting of 10 μl (250 ng) of pKT231, 6 μl of water, 2 μl of TAS buffer, and respectively 1 μl (1 unit) of dilute solutions of the enzymes EcoRI and BamHI, are incubated for 120 minutes at 37° C. and, to stop the reaction, heated for 15 minutes to 68° C. Subsequently respectively 10 μl of the two restriction batches are mixed, combined with 50 μl of water, 8 μl of 10-fold concentrated ligation buffer and 2 μl (2 units) of T4-DNA ligase, and incubated for 16 hours at 14° C. A mixture is prepared from 0.2 ml of competent cells of E. coli LE392, produced according to the process known in the literature by T. J. Silhavy et al. (Experiments with Gene Fusions, Cold Spring Harbor Laboratory, Cold Spring Harbor, N.Y., 1984),and 10 μl of the ligation batch, left on ice for 40 minutes, heated to 42° C. for 3 minutes, mixed with 2 ml of LB medium, and incubated at 37° C. for 60 minutes. Portions of 50 μl to 200 μl are spread on LB agar plates containing 50 μg/ml of kanamycin. The plates are incubated at 37° C. for 16 hours.

(c) Identification of Recombinant Plasmids

The thus-obtained kanamycin-resistant clones are spread in parallel on two LB agar plates, one of which contains 25 μg/ml of streptomycin, the other 50 μg/ml of kanamycin. The plasmid DNA is isolated from clones proving to be streptomycin-resistant in this test, in accordance with the instant method by T. Maniatis et al. (see above). Restriction of the DNA with XhoI and subsequent electrophoretic separation of the DNA fragments in a 0.7% agarose gel permit identification of recombinant plasmids yielding two XhoI fragments having the sizes of 3.0 and 9.7 kilobases. When cutting the two plasmids simultaneously with EcoRI and BamHI, electrophoretic analysis yields two fragments having the sizes of 1.5 and 11.2 kilobases. The thus-identified plasmids are recombinants from the large EcoRI/BamHI fragment of pKT231 and the 1.5-kilobase EcoRI/BamHI fragment stemming from the insert DNA of plasmid pKJS32. They are called pKJEΔB130.

EXAMPLE 7

Production of Plasmid pKJS(X)630

(a) Isolation of Plasmid pKJSB330

The clone of E. coli S17-1, obtained in Example 4 and containing the recombinant plasmid pKJS330, is cultured in 400 ml of LB medium with an addition of 50 μg/ml of kanamycin at 37° C. for 16 hours, and the plasmid DNA is isolated from the centrifuged cells by alkaline lysis according to T. Maniatis et al. (see above).

(b) Removal of a BamHI/XbaI Fragment from Plasmid pKJSB330

A reaction mixture consisting of 20 μl (1 μg) of pKJSB330, 15 μl of water, 4 μl of TAS buffer, 0.5 μl (2 units) of dilute XbaI solution, and 0.5 μl (2 units) of dilute BamHI solution is incubated at 37° C. for 120 minutes. Then 20 μl of buffered phenol according to T. Maniatis et al. (see above) is added, the batch is mixed, then again blended after adding 20 μl of chloroform : isoamyl alcohol (24:1), and removed by centrifuging. The top aqueous phase is taken off and mixed with 120 μl of cold ethanol of a temperature of −20° C. The mixture is stored at −20° C. for 30 minutes and then removed by centrifuging. The precipitated DNA is washed with cold 70% strength ethanol, dried under vacuum, and taken up in 20 μl of Klenow reaction solution [20 mM Tris-HCl, pH 8.0, 7 mM MgCl$_2$, 10 U/ml DNA polymerase I (=Klenow enzyme)]. After preliminary incubation at 37° C. for 5 minutes, 2 μl of a solution of all four deoxynucleotide triphosphates (0.125 mM ATP, 0.125 mM CTP, 0.125 mM GTP, 0.125 mM TTP, Pharmacia) is added and incubation is continued for another 5 minutes. Then the batch is mixed with 80 μl of ligation buffer containing 25 U/ml of T4-DNA ligase and left at room temperature for 6 hours. Then the mixture is incubated at 14° C. for 16 hours, 0.2 ml of a suspension of competent cells of E. coli S17-1 prepared according to the method by T. J. Silhavy et al. (Experiments with Gene Fusions, Cold Spring Harbor Laboratory, Cold Spring Harbor, N.Y., 1984) is mixed with 10 μl of the ligation batch, transformed, after 40 minutes of incubation on ice, by heat treatment (3 minutes, 42° C.), mixed with 2 ml of LB medium, and incubated at 37° C. for 60 minutes. Then portions of 50 to 200 μl of the cell suspension are spread on LB agar plates containing 50 μg/ml of kanamycin. The plates are incubated at 37° C. for 16 hours.

(c) Identification of the Shortened Plasmids

From the thus-obtained kanamycin-resistant clones, the plasmid DNA is isolated by the conventional instant method of alkaline lysis according to T. Maniatis et al. (see above). By restriction of the plasmids with SmaI and subsequent electrophoretic separation of the DNA fragments in a 0.7% agarose gel, plasmids are identified which have lost the DNA segment between the BamHI scission site and the XbaI scission site on the insert of pKJSB330. These plasmids yield, in the restriction analysis, two SmaI fragments having a length of 2.6 and 9.9 kilobases and are called pKJS(X)630. They are thus to be clearly distinguished from the starting product pKJSB330.

EXAMPLE 8

Production of Plasmids pTJSS'035 and pTJSS'036

(a) Isolation of Plasmids pT7-5, pT7-6 and pKSJ32

Two strains of E. coli HMS174, one of which contains the plasmid pT7-5, the other the plasmid pT7-6, are cultured in respectively 400 ml of LB medium according to T. Maniatis et al. (see above) with an addition of 50 μg/ml of ampicillin at 37° C. for 16 hours. From the centrifuged cells, the plasmid DNA is isolated by the known method of alkaline lysis by T. Maniatis. Isolation of pKJS32 is described in Example 5.

(b) Cloning of the SacI/SalI Fragments from pKJS32 in pT7-5 and pT7-6

A reaction mixture (A), consisting of 20 μl (1 μg) of pKJS32, 15 μl of water, 4 μl of TAS buffer, and respectively 0.5 μl (2 units) of the enzymes SacI and SalI, is incubated for 120 minutes at 37° C. Two further reaction mixtures, consisting either of 2 μl (1 μg) of pT7-5 (B) or 2 μl (1 μg) of pT7-6 (C), 15 μl of water, 2 μl of TAS buffer, and respectively 0.5 μl (2 units) of the enzymes SacI and SalI, are incubated under identical conditions. All three reactions are stopped by heating to 68° C. for 15 minutes. Respectively 13 μl of the restriction batch (A) (pKJS32) is mixed with 7 μl of the restriction batch (B) (pT7-5) and, respectively, 7 μl of the restriction batch (C) (pT7-6). The two mixtures are combined with respectively 50 μl of water, 8 μl of 10-fold concentrated ligation buffer, and 2 μl (2 units) of T4-DNA ligase. Both ligation batches are incubated at 14° C. for 16 hours. Respectively 0.2 ml of competent cells of E. coli LE392, prepared according to the procedure by T. J. Silhavy et al. (Experiments with Gene Fusions, Cold Spring Harbor Laboratory, Cold Spring Harbor, N.Y., 1984), is mixed with respectively 10 μl of the ligation batches, left on ice for 40 minutes, heated to 42° C. for 3 minutes, mixed with 2 ml of LB medium, and incubated at 37° C. for 60 minutes. Portions of 50 μl to 200 μl are spread on LB agar plates containing 50 μg/ml of ampicillin. The plates are incubated at 37° C. for 16 hours.

(c) Identification of Recombinant Plasmids

The plasmid DNA is isolated from the resultant ampicillin-resistant clones by the known instant method of alkaline lysis according to T. Maniatis et al. (see above). By restriction of the plasmids with BglII and BamHI, as well as by dual restriction with BamHI and HindIII and subsequent electrophoretic separation of the fragments in a 0.7% agarose gel, plasmids are identified consisting of one of the two vector plasmids pT7-5 or pT7-6 and the small SacI/SalI fragment of pKJS32. These recombinant plasmids yield in this case, with pT7-5 being the starting material, two BglII fragments having a size of 3.0 kilobases and 2.2 kilobases, a BamHI fragment of a size of 5.2 kilobases, and two BamHI/HindIII fragments having the sizes of 3.2 and 2.0 kilobases, and they are called pTJSS'035. In case of pT7-6 as the starting material, two BglII fragments are obtained of a size of 2.8 kilobases and 2.2 kilobases, a BamHI fragment of a size of 5.0 kilobases, and two BamHI/HindIII fragments of the sizes 3.0 kilobases and 2.0 kilobases; they are called pTJSS'036. The recombinant plasmids thus differ clearly from their starting products pKJS32 and pT7-5 or pT7-6.

EXAMPLE 9

Preparation of Plasmids pTJS'B435 and pTJS'B436

(a) Isolation of Plasmids pT7-5, pT7-6 and pKJSB330

Isolation of pT7-5 and pT7-6 has been described in Example 8; the isolation of pKJSB330 has been disclosed in Exampel 7.

(b) Cloning of the Short SalI/BamHII Fragment from pKJSB330 in pT7-5 and pT7-6

A reaction mixture (A), consisting of 40 μl (2 μg) of pKJSB330, 5 μl of TAS buffer, and respectively 2.5 μl (4 units) of dilute solutions of the enzymes SalI and BamHI, is incubated at 37° C. for 120 minutes. Two further reaction mixtures, consisting of 2 μl (1 μg) of pT7-5 (B) and, respectively, 2 μl (1 μg) of pT7-6 (C), 20 μl of water, 3 μl of TAS buffer, and respectively 2.5 μl (4 units) of dilute solutions of the enzymes SalI and BamHI, are incubated under identical conditions. The reactions are stopped by heating to 68° C. for 15 minutes. The entire restriction batch (A) (pKJSB330) is separated by electrophoresis in an agarose gel [0.7% of agarose in TBE buffer according to T. Maniatis et al. (see above) containing 0.5 μg/ml of ethidium bromide, according to T. Maniatis et al. (see above)]. Of the two DNA bands visible under UV light (300 nm), the shorter band of 2.0 kilobases is isolated from the gel by the method of DEAE membrane elution in the following way: A suitably dimensioned section of a DEAE membrane (Schleicher and Schuell, S & S NA-45) is placed into a cut 1–2 mm below the band to be eluted. The electrophoresis is continued until the respective band has been entirely absorbed by the membrane. The membrane is then removed from the gel and washed for 10 minutes with 10 ml of NET buffer (150 mM NaCl, 0.1 mM EDTA, 20 mM Tris-HCl, pH 8.0). The washed membrane is incubated in 150 µl of HNET buffer (1 M NaCl, 0.1 mM EDTA, 20 mM Tris-HCl, pH 8.0) for 30 minutes at 68° C. The solution is removed and the membrane incubated another 10 minutes with 50 µl of HNET buffer. The combined elution solutions (200 µl) are diluted with 200 µl of water, mixed with 800 µl of cold (−20° C.) ethanol, and stored at −20° C. for 30 minutes. The precipitated DNA is centrifuged and the precipitate taken up in 90 µl of water. After adding 10 µl of 3-molar sodium acetate solution according to T. Maniatis et al. (see above), the mixture is reprecipitated with 200 µl of cold ethanol (30 minutes, −20° C.), centrifuged, the precipitate washed with cold 70% ethanol, dried under vacuum, and taken up in 80 µl of ligation buffer. Of this mixture, respectively 40 µl is combined with 3 µl (100 ng) of the restriction batch (B) (pT7-5) and, respectively, 3 µl (100 ng) of the restriction batch (C) (pT7-6), and 2 µl (1 unit) of T4-DNA ligase, and incubated at 14° C. for 16 hours. An amount of 0.2 ml of competent cells of E. coli LE 392, prepared according to the method by T. J. Silhavy et al. (Experiments with Gene Fusions, Cold Spring Harbor Laboratory, Cold Spring Harbor, N.Y., 1984), is mixed with 15 µl of the ligation batch, left on ice for 40 minutes, heated to 42° C. for 3 minutes, mixed with 2 ml of LB medium, and incubated at 37° C. for 60 minutes. Portions of 50 µl to 200 µl are spread on LB agar plates containing 50 µg/ml of ampicillin. The plates are incubated at 37° C. for 16 hours.

(c) Identification of Recombinant Plasmids

The DNA is isolated from the resultant ampicillin-resistant clones according to the known instant method of alkaline lysis by T. Maniatis et al. (see above). Restriction of the plasmids with EcoRI and subsequent electrophoretic separation of the fragments in a 0.7% agarose gel afford identification of plasmids containing the short SalI/BamHI fragment from pKJSB330 in one of the two vector plasmids. Recombinant plasmids with pT7-5 as the starting product yield two EcoRI fragments of 3.0 kilobases and 1.5 kilobases in size and are called pTJS'B435; those with pT7-6 as the starting material yield two EcoRI fragments of 2.8 kilobases and 1.5 kilobases in size and are called pTJS'B436.

EXAMPLE 10

Production of Plasmids pTJS'X535 and pTJS'X536

(a) Isolation of Plasmids pT7-5, pT7-6 and pTJSS'035

E. coli LE392 containing the plasmid pTJSS'035 produced in Example 8 is cultured in 400 ml of LB medium with an addition of 50 µg/ml of ampicillin at 37° C. for 16 hours. From the centrifuged cells, the plasmid DNA is isolated according to T. Maniatis et al. (see above). Isolation of pT7-5 and pT7-6 has been set forth in Example 8.

(b) Cloning of the Short SalI/XbaI Fragment from pTJSS'035 in pT7-5 and pT7-6

A reaction mixture (A), consisting of 6 µl (3 µg) of pTJSS'035, 15 µl of water, 3 µl of TAS buffer, and respectively 2 µl (5 units) of dilute solutions of the enzymes XbaI, SalI and BamHI, is incubated at 37° C. for 120 minutes. Two further reaction mixtures, consisting of either 2 µl (1 µg) of pT7-5 (B) or 2 µl (1 µg) of pT7-6 (C), 23 µl of water, 3 µl of TAS buffer, and respectively 1 µl (2.5 units) of dilute solutions of the enzymes XbaI and SalI, are incubated in the same way. The reactions are stopped by heating to 68° C. for 15 minutes. In two different ligation batches, respectively 5 µl (500 ng) of the restriction batch (A) (pTJSS'035) is mixed with either 15 µl of restriction batch (B) (pT7-5) or 15 µl of restriction batch (C) (pT7-6), 50 µl of water, 8 µl of ligation buffer, and 2 µl (2 units) of T4-DNA ligase, and incubated at 14° C. for 16 hours. A mixture is prepared from 0.2 ml of competent cells of E. coli LE392, prepared according to the method by T. J. Silhavy et al. (Experiments with Gene Fusions, Cold Spring Harbor Laboratory, Cold Spring Harbor, N.Y., 1984) and 15 µl of the ligation batch, left on ice for 40 minutes, heated to 42° C. for 3 minutes, mixed with 2 ml of LB medium, and incubated at 37° C. for 60 minutes. Portions of 50 µl to 200 µl are spread on LB agar plates containing 50 µg/ml of ampicillin. The plates are incubated at 37° C. for 16 hours.

(c) Identification of Recombinant Plasmids

From the thus-obtained ampicillin-resistant clones, the plasmid DNA is isolated according to T. Maniatis et al. (see above). By restriction with the enzymes SmaI and EcoRI, as well as by dual restriction with EcoRI and SalI, plasmids are identified which contain the short, 1.4-kilobase SalI/XbaI fragment from pTJSS'035 in one of the two vector plasmids pT7-5 and, respectively, pT7-6. Recombinant plasmids with pT7-5 as the starting material yield two EcoRI fragments 3.0 and 0.8 kilobases in size, two SmaI fragments of the sizes 2.4 and 1.4 kilobases, and three EcoRI/SalI fragments of the sizes 2.4, 0.8 and 0.6 kilobases; they are called pTJS'X535. Recombinant plasmids with pT7-6 as the starting material yield two EcoRI fragments of the sizes of 2.8 and 0.8 kilobases, two SmaI fragments having the sizes of 2.2 and 1.4 kilobases, and three EcoRI/SalI fragments having the sizes 2.2, 0.8 and 0.6 kilobses; they are called pTJS'X536. The recombinant plasmids thus differ unequivocally from their starting materials.

EXAMPLE 11

Preparation of Plasmid pTJS'X535omega (a) Isolation of Plasmids pTJS'X535 and pDOC37

Two E. coli strains LE392, one of which contains the plasmid pTJS'X535 prepared in Example 10, the other the plasmid pDOC37, are cultured in respectively 400 ml of LB medium with an addition of 50 µg/ml of ampicillin at 37° C. for 16 hours. The plasmid DNA is isolated from the centrifuged cells in accordance with T. Maniatis et al. (see above). The plasmid pDOC37 contains the omega fragment between two EcoRI restriction sites. Instead of pDOC37, it is likewise possible to utilize, as a source for the omega fragment, the plasmid pHP45omega described by Prentki and Krisch, 1984, in Gene 29 : 103.

(b) Cloning of the Omega Fragment from pDOC37 into the BglII Site of pTJS'X535

Two reaction mixtures, one of which consists of 2 µl (1 µg) of pTJS'X535, 14 µl of water, 2 µl of TAS buffer, and 2 µl (3 units) of BglII, the other of which consists of 2 µl (2 µg) of pDOC37, 14 µl of water, 2 µl of TAS buffer, and 2 µl (4 units) of a dilute BamHI solution, are incubated at 37° C. for 120 minutes. The reactions are stopped by heating to 68° C. for 15 minutes. Respectively 10 µl of both restriction batches are combined and mixed with 80 μl of ligation buffer and 1 μl (1 unit) of T4-DNA ligase. The ligation batch is incubated at 14° C. for 16 hours. An amount of 0.2 ml of competent cells of E. coli LE 392, prepared according to T. J. Silhavy et al. (Experiments with Gene Fusions, Cold Spring Harbor Laboratory, Cold Spring Harbor, N.Y., 1984), is mixed with 10 μl of the ligation batch, left on ice for 40 minutes, heated to 42° C. for 3 minutes, mixed with 2 ml of LB medium, and incubated at 37° C. for 60 minutes. Portions of 50 μl to 200 μl are spread on LB agar plates containing 50 μg/ml of ampicillin and 80 μg/ml of spectinomycin. The plates are incubated at 37° C. for 16 hours. By selection with spectinomycin, it is ensured that all growing clones contain a plasmid with the omega fragment since the latter contains the gene for expression of spectinomycin resistance.

(c) Identification of Recombinant Plasmids

The plasmid DNA is isolated from the thus-obtained ampicillin- and spectinomycin-resistant clones according to T. Maniatis et al. (see above). By restriction with HindIII, the recombinant plasmids are identified. If three HindIII fragments are thus obtained having the sizes of 0.6, 2.0 and 3.2 kilobases, these involve derivatives of pTJS'X535 which have the omega fragment built in at the previous BglII scission site. By ligation of the compatible overlapping ends of the BglII and BamHI fragments, the restriction sites BglII and BamHI at the linkage point are lost. These recombinant plasmids are called pTJS'X535omega.

EXAMPLE 12

Production of Phages MJSS'030 and MJSS'031

(a) Isolation of Plasmid pKJS32 and the Double-Strand Forms of Phages M13tg130 and M13tg131

The strain E. coli JM101 [J. Messing et al., Nucl. Acids Res. 9 : 309 (1981)) as well as double-strand DNA of the vectors M13tg130 and M13tg131 [M. P. Kieny et al., Gene 26 : 91 (1983)] can be obtained from Amersham Buchler GmbH & Co. KG, Braunschweig. Double-strand DNA can also be obtained according to the following method: 0.2 ml of competent cells of E. coli JM101, produced according to T. J. Silhavy et al. (Experiments with Gene Fusions, Cold Spring Harbor Laboratory, Cold Spring Harbor, N.Y., 1984) are transformed with single-strand or double-strand DNA of the M13 vectors according to a process known from the literature, mixed with 3 ml of melted (45° C.) H-Top agar (10 g/l of tryptone, 8 g/l of NaCl, 8 g/l of agar), and poured on H-agar plates (10 g/l of tryptone, 8 g/l of NaCl, 12 g/l of agar). The cooled plates are incubated at 37° C. for 16 hours. 2 ml of TY medium (16 g/l of tryptone, 10 g/l of yeast extract, 5 g/l of NaCl) is inoculated with 20 μl of an overnight culture (16 hours, 37° C.) of E. coli JM101 in TY medium and a single plaque of the H-agar plate. After 16 hours of growth at 37° C., the phage-infected cells, together with a fresh overnight culture of E. coli JM101, are transferred by inoculation into 400 ml of TY medium and cultured for 16 hours at 37° C. From the centrifuged cells, the double-strand DNA is isolated according to T. Maniatis et al. (see above). Isolation of plasmid pKJS32 has been described in Example 5.

(b) Cloning of the SacI/SalI Fragment from pKJS32 into M13tg130 and M13tg131

A reaction mixture (A), consisting of 30 μl (1.5 μg) of pKJS32, 20 μl of water, 6 μl of TAS buffer, and respectively 2 μl (4 units) of dilute solutions of the enzymes SacI and SalI, is incubated at 37° C. for 120 minutes. Two further reaction mixtures, consisting of 10 μl (300 ng) of double-strand DNA of M13tg131(B) or M13tg131 (C), 25 μl of water, 4 μl of TAS buffer, and respectively 0.5 μl (1 unit) of dilute solutions of the enzymes SacI and SalI, are incubated in the same way and heated, for stopping the reaction, to 68° C. for 15 minutes. The entire restriction batch (A) is separated by electrophoresis in an agarose gel [0.7% agarose, 0.5 μg/ml of ethidium bromide in TBE buffer according to T. Maniatis et al. (see above)]. Of the two bands visible under UV light, the smaller SacI/SalI band of 2.8 kilobases is isolated by means of a DEAE membrane from the gel in the same way as has been described for the 2.0-kilobase band in Example 9. The DNA is finally taken up in 80 μl of water; of this amount, respectively 40 μl is combined with 20 μl of the restriction batches (A) (M13tg103) and, respectively, (B) (M13tg131) and 40 μl of water, mixed with 100 μl of buffered phenol/chloroform according to T. Maniatis et al. (see above), and centrifuged. The top aqueous phases are removed and, after adding 10 μl of 3-molar sodium acetate solution according to T. Maniatis et al. (see above), mixed with respectively 200 μl of cold (−20° C.) ethanol. The mixtures are left at −20° C. for 30 minutes, subsequently centrifuged, the precipitates are washed with cold 70% ethanol, dried under vacuum, and taken up in 40 μl of ligation buffer. The two batches are combined with respectively 1 μl (1 unit) of T4-DNA ligase and incubated at 14° C. for 16 hours. Respectively 0.2 ml of competent cells of E. coli JM101, prepared according to T. J. Silhavy et al. (Experiments with Gene Fusions, Cold Spring Harbor Laboratory, Cold Spring Harbor, N.Y., 1984), is mixed with 10 μl of the ligation batches, left on ice for 40 minutes, heated to 42° C. for 3 minutes, and combined with respectively 3 ml of melted (45° C.) H-Top agar. The mixtures are combined with respectively 40 μl of IPTG (100 mM) and 40 μl of Xgal (2% in dimethyl-formamide) and poured on H-agar plates. The cooled plates are incubated at 37° C. for 16 hours.

(c) Identification of Recombinant Phages

Among the thus-obtained plaques, those stem from recombinant phages which do not exhibit a blue coloration. For further identification, the double-strand and single-strand DNA is isolated from the colorless plaques according to methods known from the literature, compiled in "M13 Cloning and Sequencing Handbook" by Amersham. Restriction of the double-strand DNA with BglII and subsequent electrophoretic separation of the DNA fragments identify derivatives of M13gt130 and, respectively, M13tg131 which contain the short SacI/SalI fragment from pKJS32. Recombinant phages with M13tg130 as the vector yield three BglII fragments of the sizes 0.7, 2.2 and 7.1 kilobases and are denoted as MJSS'030; those with M13tg131 yield four BglII fragments of the sizes 0.6, 0.7, 2.2 and 6.6 kilobases and are called MJSS'031. They differ accordingly clearly from their starting products.

EXAMPLE 13

Production of the tfdA Mutants Alcaligenes eutrophus JMP134:Tn5-2 and JMP134:Tn5-4

(a) Transposon Mutagenesis of Alcaligenes eutrophus JMP134

10 ml of PYE mdium (3 g/l of peptone, 3 g/l of yeast extract) is inoculated with 0.5 ml of an overnight culture (16 hours, 30° C.) of Alcaligenes eutrophus JMP134 (R. H. Don et al., J. Bacteriol. 145 : 681 (1981)] and shaken for 8 hours at 30° C. 10 ml of LB medium according to T. Maniatis et al. (see above) is inoculated with 0.1 ml of an overnight culture of *E. coli* S17-1 [Biotechnology 1 : 784 (1983)] containing the plasmid pSUP2021, and shaken for 5 hours at 37° C. Subsequently, the optical density at a wavelength of 600 nm is determined in a photometer for both cultures. The cultures are mixed in a proportion of 1 : 1 with respect to their optical density and 1.5 ml of the mixture is distributed on a PYE agar plate [R. H. Don et al., J. Bacteriol. 145 : 681 (1981)]. The plate is incubated for 16 hours at 30° C. Subsequently the bacteria are rinsed off the plate with 1.5 ml of sterile 0.7% NaCl solution and the bacterial suspension is diluted in two steps with 0.7% NaCl solution respectively 1 : 10 (0.1 ml+0.9 ml). Of each dilution, portions of 50 μl, 100 μl, 200 μl and 400 μl are spread on minimal agar plates (1.6 g/l of dipotassium hydrogen phosphate, 0.4 g/l of potassium dihydrogen phosphate, 1 g/l of ammonium sulfate, 0.05 g/l of magnesium sulfat x 7 water, 0.01 g/l of iron(II) sulfate x 7 water, 15 g/l of agar), these plates additionally containing 2 g/l of fructose and 380 μg/ml of kanamycin. The plates are incubated at 30° C. for 3 to 7 days.

(b) Testing the Transposon-Containing Strains for 2,4-D Degradation

The thus-obtained kanamycin-resistant clones represent progeny of the strain JMP134 which have integrated the transposon Tn5 in a stable fashion in their genome. They are spread in parallel on two minimal agar plates, one of which contains. 1 mM of 2,4-dichlorophenoxyacetic acid, sodium salt (2,4-D), the other of which contains 2 g/l of fructose and 380 μg/ml of kanamycin. The plates are incubated for 3 days at 30° C. Strains exhibiting mutation in one of the genes responsible for 2,4-D degradation cannot utilize 2,4-D as a growth substrate (2,4-D-negative). They occur at a frequency of 0.1–1%, based on the entirety of transposon-containing, kanamycin-resistant clones.

(c) Identification of the Gene Defect of the 2,4-D-Negative Mutants

The thus-obtained 2,4-D-negative mutants are spread in parallel on two minimal agar plates, one of which contains 2 mM of 3-chlorobenzoic acid, sodium salt (3-CB), the other 2 g/l of fructose and 380 μg/ml of kanamycin. The plates are incubated for 3 days at 30° C. 2,4-D-negative transposon mutants of the strain JMP134 exhibiting mutation in the genes tfdc, tfdD and tfdE of 2,4-D degradation cannot utilize 3-CB as a growth substrate (3-CB-negative), as could be shown by Don et al. [J. Bacteriol. 161 : 85 (1985)]. Mutants in the genes tfdA and tfdB, in contrast thereto, can grow on 3-CB as the sole carbon source (3-CB-positive). Transposon mutants proving to be 3-CB-positive in this test are accordingly further investigated by means of an enzyme test for defects in the genes tfdA or tfdB. For this purpose, the strains are cultured in 250 ml of minimal medium (as above, without agar) with an addition of 15 mM of sodium pyruvate and 1 mM of 3-CB for 16 hours at 30° C. The cells are harvested by centrifuging at 4° C., washed three times in 10 ml of cold (4° C.) minimal medium (without carbon source), and recentrifuged, and finally suspended in such a quantity of minimal medium that an optical density of 30 is obtained at 420 nm. For the enzyme test of 2,4-D-monooxigenase and, respectively, 2,4-dichlorophenolhydroxylase, 1 volume proportion of the cell suspension is mixed with 9 parts by volume of an oxygen-saturated minimal medium so that an optical density of 3 results at 420 nm. With the aid of a commercially available oxygen electrode, the oxygen absorption is then observed over 10 minutes without adding substrate. Subsequently, 2,4-D is added to a final concentration of 1 mM, or 2,4-dichlorophenol is added to a final concentration of 0.2 mM, and the decrease in oxygen concentration over a period of 20 minutes is observed. By means of this test, tfdA mutants can be distinguished from all other types of mutations, as well as from the wild-type strain JMP134: They show no increase whatever in oxygen consumption after addition of 2,4-D, whereas, upon addition of 2,4-dichlorophenol, a significant rise in oxygen absorption occurs. The wild-type strain, as well as tfdB mutants, show increased oxygen consumption after addition of 2,4-D as the substrate and thus indicate intact 2,4-D-monooxygenase. The two transposon mutants JMP134:Tn5-2 and JMP134:Tn5-4 are two 2,4-D-negative, 3-CB-positive mutants with a detectable 2,4-dichlorophenolhydroxylase, but without detectable 2,4-D-monooxygenase. They can thus be identified as tfdA mutants. This designation is confirmed by additional experiments described in the examples below.

EXAMPLE 14

Expression of Cloned tfdA Genes in Gram-Negative Bacteria Other Than *E. coli*

(a) Preparation of Donor Strains for Conjugative Transfer of tfdA-Containing Plasmids The plasmids constructed on the basis of mobilizable vectors with a wide hostrange, such as pVK101[V. C. Knauf et al., Plasmid 8 :45 (1982)], pGSS33 [G. S. Sharpe, Gene 29 : 93 (1984)], and pKT321 [M. Bagdasarian et al., Current Topics in Microbiology and Immunology 96 : 74 (1982)], the preparation of which has been disclosed in Examples 1 through 7, can be transferred from the mobilizing strain *E. coli* S17-1 [Biotechnology 1 : 784 (1983)] by conjugation to other gram-negative bacteria, such as, for example, *Alcaligenes eutrophus* and *Pseudomonas putida*. For this purpose, they must first be introduced by transformation into *E. coli* S17-1 unless they have already been cloned in this strain. To this end, the plasmid DNA is isolated from the clones of *E. coli* LE392 containing the respective plasmid, in accordance with T. Maniatis et al. (see above). A mixture is made up of 0.2 ml of competent cells of *E. coli* LE392 produced according to T. J. Silhavy et al. (Experiments with Gene Fusions, Cold Spring Harbor Laboratory, Cold Spring Harbor, N.Y., 1984) and 1 μl of the isolated plasmid DNA, left on ice for 40 minutes, heated to 42° C. for 3 minutes, mixed with 2 ml of LB medium, and incubated at 37° C. for 60 minutes. Portions of 50 μl to 200 μl are spread on LB agar plates containing the corresponding antibiotic suitable for selection. The plates are incubated at 37° C. for 16 hours.

(b) Conjugative Transfer

A thus-obtained strain of *E. coli* S17-7 containing one of the plasmids described in Examples 1–7 is cultured for 16 hours at 37° C. in 5 ml of LB medium containing an antibiotic suitable for selection. As the recipient, one of the two tfda mutants isolated in Example 13 (case A), the pJP4-free strain *Alcaligenes eutrophus* JMP222 [R. H. Don et al., J. Bacteriol. 145 : 681 (1981)] (case B), or Pseudomonas spec. B13 [E. Dorn et al., Arch. Microbiol.99 : 61 (1974)] (case C) are cultured in 5 ml of PYE medium (3 g/l of peptone, 3 g/l of yeast extract) at 30° C. for 16 hours. The cells of the donor strain are centrifuged and suspended in double the volume of PYE medium. The suspension of the donor cells and the culture of the recipient are mixed in equal parts. 100 μl of the mixture is pipetted onto a membrane filter (Millipore HA 0.45 μm) located on the surface of a PYE agar plate. Subsequently, the plate is incubated for 6 hours at 30° C. Then the cells are rinsed off the filter with 1 ml of 0.7% NaCl solution and the cell suspension is diluted in 7 steps respectively 1 : 10 (0.1 ml+0.9 ml) with 0.7% NaCl solution. Of each dilution, 100 µl is spread on a minimal agar plate containing one of the following growth substrates: 1 mM 2,4-D in case A (tfda mutant), 4 mM phenoxyacetic acid-Na in case B (*Alcaligenes eutrophus* JMP222) or 1 mM 4-chlorophenoxyacetic acid-Na in case C (*Pseudomonas* B13). The plates are incubated in case A for 14 days, in cases B and C for 4 days, at 30° C.

(c) Properties of the Newly Formed Strains

Mobilizable plasmids with a wide host range from the aforementioned group, containing an intact tfda gene, render, after conjugative transfer, the respective recipient strain capable of synthesizing a functional 2,4-D-monooxygenase. This leads in case A (tfda mutant) to complementation of the mutation and thus to restoration of the wild-type property with respect to utilization of 2,4-D, i.e. strains are produced which are 2,4-D-positive, growing on 2,4-D-minimal agar plates. The 2,4-D-mono-oxygenase coded by tfdA is furthermore capable of enzymatic conversion of, besides 2,4-D, also the compounds chemically related to 2,4-D, phenoxyacetic acid and 4-chlorophenoxyacetic acid, thus forming as the products phenol and, respectively, 4-chlorophenol. Since the strain *Alcaligenes eutrophus* JMP222 does exhibit genes for the complete metabolizing of phenol, there result after conjugative transfer of tfda-containing plasmids, in case B, strains having the novel property of utilizing phenoxyacetic acid as growth substrate. In the same way, a tfdA-containing plasmid renders a Pseudomonas B13 equipped with this plasmid and having complete degradation pathways for phenol and 4-chlorophenol, capable of growing on the substrates phenoxyacetic acid and 4-chlorophenoxyacetic acid (case C). The test for utilization of a specific substrate as described above is especially suitable for the confirmation of expression of the tfdA gene by DNA fragments cloned in mobilizable broad host range vectors, and the shortened derivatives of these fragments, the production of which has been set forth in Examples 1–7. It turns out that the plasmids pVJH21, pGJS3, pKJS31, pKJS32, pKJSE330, pKJS32RHAS' and pKJS(X)630 all contain an intact tfdA gene whereas the plasmid pKJEAB130 does not code an operable gene product.

EXAMPLE 15

Accumulation of tfdA-Coded 2,4-D-Monooxigenase in *E. coli*

(a) Production of Highly Productive *E. coli* Strains

The recombinant plasmids described in Examples 8, 9, 10 and 11, produced based on the vectors pT7-5 and pT7-6, constructed by Tabor, contain cloned DNA fragments following a strong promoter of phage T7. Plasmids from this group, containing an intact tfda gene in the correct orientation with respect to the promoter, can produce 2,4-D-monooxygenase in large amounts under the influence of T7-RNA polymerase expressed by the plasmid pGP1–2 [S. Tabor et al., Proc. Natl. Acad. Sci. USA 82 : 1074 (1985)] in *E. coli* K38. Since the promoter is recognized specifically only by T7-RNA polymerase, and since the latter is on the plasmid pGP1–2 under the control of a heat-sensitive lamba repressor, the synthesis of the gene product canbe induced by heat. By adding rifampicin, it is furthermore possible to inhibit the bacterial RNA polymerases. In order to produce the highly productive strains, the plasmid DNA is isolated from the plasmid-containing strains of *E. coli* LE392, obtained in Examples 8–11, according to T. Maniatis et al.

(see above). *E. coli* K38, containing the plasmid pGP1–2, is cultured for 16 hours at 30° C. in LB medium that has been combined with 50 µg/ml of kanamycin for selection oriented toward pGP1–2. From the grown culture, competent cells are produced according to the method by T. J. Silhavy et al. (Experiments with Gene Fusions, Cold Spring Harbor Laboratory, Cold Spring Harbor, N.Y., 1984). An amount of 0.2 ml of competent cells is mixed with 1 µl of the isolated DNA, left on ice for 40 minutes, heated to 37° C. for 5 minutes, mixed with 2 ml of LB medium, and incubated at 30° C. for 60 minutes. Portions of 50 µl to 200 µl are spread on LB agar plates containing 50 µg/ml of ampicillin and 50 µg/ml of kanamycin. The plates are incubated at 30° C. for 16 hours.

(b) Induced Production and Radiolabeling of the tfda Gene Product

The thus-obtained ampicillin- and kanamycin-resistant clones contain the plasmid pGP1–2 and one of the recombinant pT7 derivatives. They are cultured in 10 ml of LB medium with an addition of 50 µg/ml of ampicillin and 50 µg/ml of kanamycin at 30° C. At an optical density of 0.5, measured at 590 nm, 0.2 ml of culture is removed by centrifuging. The cells are washed in 5 ml of M9 medium according to T. Maniatis et al. (see above), again centrifuged, and finally suspended in 1 ml of M9 medium containing 20 µg/ml of thiamine and respectively 0.01% of all proteinogenic amino acids except for methionine and cysteine (18 in total). The cell suspension is shaken at 30° C. for 60 minutes; then the temperature is raised to 42° C. After 15 minutes, 10 µl of rifampicin solution (20 mg/ml in methanol) is added and the batch is left at 42° C. for another 10 minutes. Thereafter the temperature is again lowered to 30° C.; after 20 minutes the batch is combined with 10 µCi of L-($^{35}$S)methionine (Amersham, cell labeling grade) and left for 5 minutes at room temperature. The cells are subsequently removed by centrifuging, suspended in 120 µl of application buffer (60 mM of Tris-HCl, pH 6.8, 1% sodium lauryl sulfate, 1% 2-mercaptoethanol, 10% glycerol, 0.01% bromophenol blue), and heated to 95° C. for 3 minutes.

(c) Identification of Specifically Radiolabeled tfda Gene Product

The thus-obtained samples are loaded on a 12.5% strength polyacrylamide gel [U. K. Laemmli, Nature, 227 : 680 (1970)], and the entire bacterial proteins are separated electrophoretically in accordance with the method, known from the literature, described therein. After electrophoresis has been completed, the gel is stained for 30 minutes in a mixture of 2.5 g of SERVA blue G, 454 ml of methanol 92 ml of acetic acid, and 454 ml of water and then decolorized for 24 hours in a mixture of 50 ml of methanol, 75 ml of acetic acid, and 875 ml of water. The gel is dried on a filter paper (Whatman 3MM) with the aid of a commercially available gel desiccant; then autoradiography is performed according to T. Maniatis et al. (see above) with an X-ray film (Kodak Industrex AX), and the film is developed. On the autoradiogram, an individual marked protein is identified in those strains containing, besides pGP1–2, one of the plasmids pTJSS'035, pTJS'B435, pTJS'X535 or pTJS'X535omega. All of these homologous plasmids have the feature in common that the cloned fragment is transcribed by the T7-RNA polymerase toward the SalI end. In case of plasmids having the reverse orientation of the insert (pTJSS'036, pTJS'B435 and pTJS'X535), no specifically marked protein is found. By comparison with standard proteins of a known size, the molecular weight of the marked proteins is determined. This results, for the gene products expressed by pTJSS'035, pTJS'B435.and pTJS'X535, in a molecular weight of 32,000, for the gene product expressed by pTJS'X535 in a molecular weight of 29,000.

(d) Induced Production with Confirmation of Enzymatic Activity

The above-obtained strains of E. coli K38, containing pGP1–2 and one of the plasmids pTJSS'035, pTJS'B435, pTJS'X535 or pTJS'X535omega, are grown at 30° C. in 20 ml of LB medium with an addition of 50 µg/ml of ampicillin and 50 µg/ml of kanamycin. At an optical density of 1.0 at 590 nm, the temperature is increased to 42° C., and the culture is shaken for 25 minutes. Thereafter, 100 µl of rifampicin solution (20 mg/ml in methanol) is added and the culture shaken for 2 hours at 37° C. Detection of enzymatic activity of 2,4-D-monooxygenase in E. coli is carried out along the lines of the method of radioactive enzyme test described by Amy et al. [Ap$\mu$l. Env. Microbiol. 49 : 1237 (1985)], with the following modifications: The cells of an induced 20 ml culture are harvested by centrifuging, washed with 10 ml of EM medium, again centrifuged, and finally suspended in 10 ml of EM medium. The cell suspension is mixed in a 250 ml Warburg flask with 10 ml of transformation buffer, combined with 200 µg of unlabeled 2,4-D and 0.1 µCi of 2,4-dichlorophenoxy(2-$^{14}$C)acetic acid (Amersham, 55 mCi/mmol), and shaken in the sealed flask at 21° C. for 4 hours. Subsequently, 0.5 ml of beta-phenylethylamine is pipetted into the central vessel of the Warburg flask, and 2 ml of 1-molar sulfuric acid is injected into the cell suspension. After one hour of shaking at 21° C., the beta-phenylethylamine is taken up in 5 ml of counter fluid ("rotiszint 22", Roth), and the radio-activity of the sample is measured in a scintillation counter. Strains of E. coli K38 containing, besides pGP1–2, one of the plasmids pTJSS'035, pTJS'B435 or pTJS'X535 exhibit high enzyme activity in this test, whereas those with the plasmid pTJS'X535omega express no enzyme activity.

EXAMPLE 16

Determination of Base Sequence of DNA Cloned in M13

(a) Production of Deleted Phages from MJSS'030 and MJSS'031

For sequencing the 2-kilobase BamHI/SalI fragment of the recombinant phages according to the method by Sanger [Proc. Natl. Acad. Sci. USA, 74 : 5463 (1977)], a series of differently shortened phages is first produced by controlled deletion according to a process known from the literature [G. Henikoff, Gene, 28 : 351 (1984)], making it possible to determine the entire base sequence by overlapping sequencing of respectively 200 to 300 bases. For this purpose, the double-stranded DNA is isolated from strains of E. coli JM101 containing the phages MJSS'030 and, respectively, MJSS'031 produced in Example 12, in accordance with the method described therein for the phage vectors M13tg130 and M13tg131. 10 µg of double-stranded DNA of the phage MJSS'030 is cut with the enzymes PstI and SalI, 10 µg of double-stranded DNA of the phage MJSS'031 is cut with the enzymes BamHI and SacI. The restriction batches are extracted with phenol and the cut DNA is precipitated with ethanol. The subsequent digestion of DNA with exonuclease III and S1-nuclease, Klenow capping of the projecting DNA ends, and ligation take place exactly according to the method described by Henikoff, with the following change: Instead of using S1-nuclease, mung bean nuclease (Pharmacia) is utilized. Portions of 0.2 ml of competent cells of E. coli JM101 [J. Messing et al., Nucl. Acids Res. 9 : 309 (1981)], prepared according to the process by T. J. Silhavy et al. (Experiments with Gene Fusions, Cold Spring Harbor Laboratory, Cold Spring Harbor, N.Y., 1984), are combined with respectively 20 µl of the ligation batches, left on ice for 40 minutes, heated to 42° C. for 3 minutes, mixed with respectively 3 ml of melted (45° C.) H-Top agar (Example 12), and poured on H-agar plates (Example 12). The plates are incubated at 37° C. for 16 hours.

(b) Identification of Deleted Phages

E. coli JM101 is cultured in 2 ml of TY medium (Example 12) at 37° C. for 16 hours. Of this culture, 1 ml is diluted with 100 ml of TY medium, and respectively 2 ml of the diluted cell suspension is infected with one of the above-obtained plaques. The cultures are shaken at 37° C. for 5 hours and then centrifuged. From the supernatants of centrifugation, the single-strand DNA is obtained in accordance with the procedure indicated by Amersham [M13 Cloning and Sequencing Handbook, 1984]. The double-strand DNA is isolated from the centrifuged cells in accordance with T. Maniatis et al. (see above). The double-strand DNA of the shortened phages evolved from MJSS'030 is digested with BglII, that of the phages evolved from MJSS'031 with EcoRI and SalI. By subsequent electrophoretic separation of the fragments on a 2% agarose gel according to T. Maniatis et al. (see above), the size of the respective deletion is determined.

(c) Sequencing of Single-Strand DNA

The base sequence of the above-obtained single-strand DNA of the shortened phages, as well as of the single-strand DNA of MJSS'030 and MJSS'031 produced in Example 12 is determined according to the method, known from the literature, of dideoxynucleotide sequencing [Proc. Natl. Acad. Sci. USA 74 : 5463 (1977)]. In this procedure, the directions given by Amersham [M13 Cloning and Sequencing Handbook, 1984] are followed. In order to separate the DNA fragments, a gel having a length of 55 cm with a thickness increasing from 0.1 mm to 0.4 mm is utilized. The identified DNA sequences of the shortened phages are joined with the aid of a computer program [C. Queen et al., Nucl. Acids Res. 12 : 581 (1984)] at overlapping regions to a DNA sequence encompassing the entire segment between the BamHI scission site and the SalI scission site of the insert cloned in M13tg130 and, respectively, M13tg131. The base sequence is confirmed by comparison of the two thus-obtained complementary DNA strands.

(d) Properties of Sequenced DNA

With the aid of the above-mentioned computer program, all properties of the DNA are determined which result directly from the base sequence. Among these, the most important that can be cited are: the position of the recognition sites for restriction endonucleases, the location and length of the open reading frames as possible coding regions of a gene, the frequency of specific bases and their distribution, and the occurrence of certain functional DNA sequences. Analysis of the DNA sequence shows an open reading frame, the location, length and transcription direction of which coincide with the properties of the tfda gene, described in Examples 14 and 15. This frame begins at a GTG starting codon with the base No. 748 and ends upstream of a TAG stop codon with base No. 1608, and therefore has a length of 861 bases, corresponding to the length of the tfda-coded protein (Example 15). The insertion of transcription and translation stop signals into the sole BglII cutting site of the sequenced fragment, as represented by the cloning of the omega fragment in pTJS'X535

(Example 11), shortens this open reading frame by calculation to 768 bases, which coincides with the expression of a shortened and enzymatically inactive gene product by the plasmid pTJS'X535omega (Example 15).

EXAMPLE 17

Construction of plasmids for constitutive and light-induced DPAM expression in plants a) Synthesis of oligonucleotides To create a plant/bacterial hybrid gene for 2,4-dichlorophenoxyacetate monooxygenase (DPAM) the prokaryotic translation initiation codon GTG of gene tfda has to be replaced by an ATG codon. This is achieved by a synthetic double stranded oligonucleotide which is designed to fit a 5' protruding end generated by FokI 8 bp downstream from the translation initiation codon. The oligonucleotide contains a sequence reconstituting the original open reading frame for DPAM, a consensus sequence for plant translation start sites upstream from the ATG start codon (Lutcke) and a 5' protruding end compatible with the cloning site BamHI (the sequences are specified in FIG. 11). Oligonucleotides are made by an automatic synthesizer, like an Applied Biosystems 380A equipment, and purified by common methods as HPLC or preparative polyacrylamide gel electrophoresis which are described in the Applied Biosystems User Bulletin, issue No. 13, 1984 (Applied Biosystems, Foster City, Calif.).

b) Construction of a hybrid coding sequence

Pairs of complementary oligonucleotides, each consisting of 20 bases, are phosphorylated by polynucleotide kinase, annealed by shifting temperature from 60° C. to 37° C., and then ligated with pUC18 (Norrander et al., Gene 26:101, 1983) that had been digested with BamHI and SphI. The linear product is separated from an excess of oligonucleotides by agarose gel electrophoresis using DEAE membrane NA45 (Schleicher & Schuell). pTJSX535 plasmid DNA is digested with XbaI and SphI and separated by agarose gel electrophoresis. The 1.2 kb fragment containing the DPAM coding sequence is isolated from the gel by electroelution, partially digested by FokI, and repurified by agarose gel electrophoresis. DNA fragments of around 1.1 kb isolated from the gel are ligated with the linear pUC18/oligonucleotide-construction, thus linking the oligonucleotide with the truncated coding sequence of tfda (FIG. 11). Competent cells of E. coli TB1 are transformed with the recombinant DNA and clones are selected on LB-agar containing 50μg/ml ampicillin. E. coli TB1 is a derivative of strain JM101 (Yanisch-Perron et al., Gene 33:103, 1985) with the genotype: F'(traD36, proAB, laci, lacZAM15)Δ (lac, pro), SupE, thi, recA, Srl::Tn10(Tc$^r$)(Bart Barrel, personal communication). Clones containing plasmid pUJC1001 are identified by restriction analysis of isolated plasmid DNA. The correct ligation of the oligonucleotide is verified by sequence analysis of CsCl-purified pUJC1001 DNA using the dideoxy method (Sanger et al., Proc. Natl. Acad. Sci. USA 74:5463, 1977) modified for plasmid DNA as a template (Chen and Seeburg, DNA 4:165, 1985).

c) Construction of plasmids for plant expression

To fuse the new hybrid coding sequence at its 3' end to a termination and polyadenylation signal, DNA of pUJC1001 is digested with BamHI and SphI to excise the insert and then ligated with a BamHI and SphI cleaved pA5. pA5 is a pUC18 derivative that contains a 200 bp fragment of the octopine synthetase gene 3' end (OCS-polyA) (Dhaese et al., EMBO J. 2:419, 1983). The resulting plasmid pUJCO1003 is cloned in E. coli TB1 as described in section b, above.

To fuse the 5' end of the hybrid DPAM gene to the cauliflower mosaic virus (CMV) 35S promoter (Paszkowski et al., EMBO J. 3:2717, 1984), DNA of both pUJCO1003 and pA8 is digested with BamHI and SphI, mixed and ligated. The vector pA8 is based on the intermediate vector pMPK110 (Peter Eckes, Dissertation, Universität Köln, 1985) which is able to form cointegrates with disarmed Ti-plasmids of A. tumefaciens such as pGV3850kan (Jones et al., EMBO J. 4:2411, 1985). Competent cells of E. coli TB1 are transformed with the ligated DNA and clones are selected on LB agar containing 25 μg/ml streptomycin. The resulting plasmid, designated pMCJC1007 (FIG. 11), is identified by restriction analysis.

A similar construction is made using the light-inducible promoter of gene ST-LS1 (Stockhaus et al., Proc. Natl. Acad. Sci. USA 84:7943, 1987) instead of the constitutive CMV 35S promoter to form a plasmid designated pMLJC1005 (Figure not shown).

EXAMPLE 18

Expression of the DPAM gene in E. coli

For the two intermediate constructs, pUJC1001 and pUJCO1003 (FIG. 11), the DNA sequence predicts a fusion protein between the short N-terminal end of the lacZ coding region of pUC18 and the new hybrid coding sequence of the DPAM gene. This allows the expression of a functional DPAM in E. coli TB1 from the IacZ promoter. Cells of E. coli TB1 containing pUJCO1003 are induced by IPTG and activity of DPAM within these cells is measured by the radioisotopic 2,4-D assay of Example 15d. DPAM activity is found in induced cells. In a similar assay nonradioactive 2,4-D is used as a substrate and the reaction product is detected by gas chromatography (Perkins et al., Weed Science 35:12, 1987). Subsequent mass spectrometry identifies 2,4-dichlorophenol (2,4-DCP) as the reaction product of the cloned DPAM.

EXAMPLE 19

Transformation of tobacco with chimeric DPAM genes

Both constructs containing the hybrid DPAM genes in combination either with the constitutive (pMCJC1007) or with the light-inducible promoter (pMLJC1005) are mobilized from E. coli TB1 into the Agrobacterium strain C58Cl (pGV3850kan)(Jones et al., EMBO J. 4:2411, 1985) by a triparental mating (Sanchez-Serrano et al., EMBO J. 6:303, 1987) using E. coli GJ23 (Van Haute et al., EMBO J. 2:411, 1983) as a helper strain. Agrobacteria are checked by southern hybridization to contain the DPAM gene and subsequently used for leaf disc infection of Nicotiana tabacum W38. Transformation and regeneration of tobacco plants follow established procedures (Sanchez-Serrano et al., EMBO J. 6:303, 1987). Shoots are regenerated from infected leaf discs by selection on 100 μg/ml kanamycin and screened for nopaline production. Transformed shoots are rooted and then transferred to soil. RNA is isolated from leafs and analyzed by agarose gel electrophoresis and subsequent northern blot hybridization using the 1.1 kb BamHI-SphI fragment of pTJSX535 as labeled probe. Transformed plants synthesize a specifically hybridizing transcript of 1.3 kb in size.

EXAMPLE 20

Expression of the DPAM gene in tissue culture of tobacco

As 2,4-D is known to promote callus growth and to suppress shoot regeneration from explanted tobacco leaf discs in tissue culture when applied in concentrations higher than 0.1 mg/l, transgenic plants can be tested for their ability to tolerate elevated levels of 2,4-D on a synthetic "shoot regeneration" medium. This medium consists of MS (Murashige and Skoog, Physiol. Plant 15:473, 1962), 15 g/l agar, 20 g/l sucrose, 1.0 mg/l 6-benzylaminopurine and different concentrations of 2,4-D, ranging from 0.1 mg/l up to 4.0 mg/l. Leaf discs from sterile tobacco plants are placed on the agar and incubated in the light for 3 weeks. Leaf discs from transformed plants where the DPAM gene is under the control of the constitutive 35S promoter develop normal shoots on a medium containing up to 2.0 mg/l 2,4-D (FIG. 12A), whereas leaf discs from untransformed control plants (*Nicotiana tabacum* W38) do not show any differentiation on a medium containing more than 0.1 mg/l 2,4-D. This indicates that expression of the DPAM gene can result in up to 20-fold higher tolerance against 2,4-D.

EXAMPLE 21

Response to differently substituted phenoxyacetic acids

DPAM is able to degrade differently substituted phenoxyacetic acid derivatives. To show how transgenic tobacco expressing DPAM responds to the auxin activity of these compounds, the substances listed in FIG. 13 are incorporated in MS-agar together with 1.0 mg/l BAP as described in Example 20. Leaf discs of transgenic tobacco expressing DPAM under the control of the constitutive 35S promoter and tobacco W38 are placed on the media and shoots arising are counted after 18 to 21 days. FIG. 13 shows that transgenic plants express a similar tolerance to 4-CPA as to 2,4-D, a slightly reduced tolerance to MCPA and no tolerance to the tested tri-substituted phenoxyacetic acids and all tested phenoxypropionic acids.

EXAMPLE 22

Resistance of transgenic plants to the herbicidal activity of 2,4-D

Transgenic plants are transferred to soil and grown in the greenhouse. No difference in growth should be seen between untransformed and transformed tobacco. Control tobacco plants and transgenic tobacco plants are sprayed with 4 ml of a 1% aqueous solution of 2,4-D, Na-salt. With an estimated ground surface of 400 cm$^2$ per plant this roughly corresponds to an applied amount of 10 kg/ha. Doses equivalent to 3 kg/ha and 1 kg/ha 2,4-D-Na are achieved by appropriate dilution of the spray solution. Whereas 1 kg/ha totally inhibits growth of control plants, transgenic plants which express the DPAM gene under the control of the constitutive 35S promoter are resistant to up to 10 kg/ha 2,4-D-Na (FIG. 14A). Transgenic plants which express the DPAM gene under light-induction are at least resistant to 1 kg/ha 2,4-D-Na (FIG. 14B).

In the foregoing description and examples, all temperatures are set forth uncorrected in degrees Celsius and, unless otherwise indicated, all parts and percentages are by weight.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The foregoing preferred specific embodiments are, therefore, to be construed as merely illustrative and not limitative of the remainder of the disclosure in any way whatsoever.

The entire texts of all applications, patents and publications cited above, and of corresponding application P 36 29 890.5 filed Aug. 29, 1986 in the Federal Republic of Germany, are hereby incorporated by reference.

From the foregoing description, one skilled in the art can easily ascertain the essential characteristics of the invention and, without departing from the spirit and scope thereof, can make various changes and modifications of the invention to adapt it to various usages and conditions.

What is claimed is:

1. A recombinant gene, comprising a DNA sequence encoding a polypeptide having the biological activity of 2,4-D monooxygenase which is capable of being expressed in a plant, operably linked to a heterologous promoter capable of promoting the expression in a plant of a structural gene operably linked thereto.

2. A transgenic plant containing a recombinant gene of claim 1.

3. A transgenic plant of claim 2, wherein the exogenous DNA sequence encoding a polypeptide having the biological activity of 2,4-D monooxygenase which is capable of being expressed in a plant is operably incorporated into the genome of the host plant cell.

4. A recombinant gene of claim 7, wherein the DNA sequence is the structural gene sequence of FIG. 10, except that the initiation codon is ATG, a DNA sequence differing therefrom by codon degeneracy, or a DNA sequence hybridizable therewith.

5. A recombinant vector comprising a recombinant gene of claim 4.

6. A recombinant gene of claim 1, wherein the structural gene sequence is derived from *Alcaligenes eutrophus* JMP134 plasmid pJP4, DSM 3840.

7. A recombinant vector comprising a recombinant gene of claim 6.

8. A recombinant vector comprising a recombinant gene of claim 1.

9. Plasmids pVJH21, pGJS3, pKJS31, pKJS32, pKJSB330, pKJS(x)630 and pKJS32RHΔS', each a vector of claim 8.

10. Plasmids pTRJS'B435, pTJS'B436, pTJSS'035, pTJSS'036, pTJS'x535 and pTJS'x536, each a vector of claim 8.

11. A bacterial strain transformed with a vector of claim 8.

12. A method of preparing a polypeptide having the biological activity of 2,4-D-monooxygenase, comprising culturing a cell of claim 11.

13. A transgenic microorganism or plant comprising cells of a microorganism or plant transformed with a vector of claim 8.

14. A method of preparing a polypeptide having the biological activity of 2,4-D-monooxygenase, comprising culturing a transgenic plant of claim 13.

15. A method of claim 14, whereby the plant is protected against growth inhibition caused by treatment of the plant with a substituted phenoxyacetic acid.

16. A method of claim 15, wherein the substituted phenoxyacetic acid is 2,4-dichlorophenoxyacetic acid, 4-chlorophenoxyacetic acid or (2-methyl-4-chlorophenoxy) acetic acid.

* * * * *

UNITED STATES PATENT AND TRADEMARK OFFICE
CERTIFICATE OF CORRECTION

PATENT NO. : 6,153,401
APPLICATION NO. : 07/322604
DATED : November 28, 2000
INVENTOR(S) : Wolfgang R. Streber et al.

It is certified that error appears in the above-identified patent and that said Letters Patent is hereby corrected as shown below:

Column 32, Claim 4, lines 27-33:

"A recombinant gene of claim 7, wherein the DNA sequence is
   the structural gene sequence of FIG. 10, except that the initiation codon is ATG,
   a DNA sequence differing therefrom by codon degeneracy, or
   a DNA sequence hybridizable therewith."

should read:

--A recombinant gene of claim 1, wherein the DNA sequence is
   the structural gene sequence of FIG. 10, except that the initiation codon is ATG,
   a DNA sequence differing therefrom by codon degeneracy, or
   a DNA sequence hybridizable therewith or its complement, wherein the sequence or
     its complement codes for a polypeptide having said biological activity.--

Signed and Sealed this
Thirty-first Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,153,401 | Page 1 of 3 |
| APPLICATION NO. | : 07/322604 | |
| DATED | : November 28, 2000 | |
| INVENTOR(S) | : Wolfgang R. Streber et al. | |

It is certified that error appears in the above-identified patent and that said Letters Patent is hereby corrected as shown below:

Delete Drawing Sheets 13 of 17 and 15 of 17 and substitute therefore the attached Drawing Sheets 13 of 17 and 15 of 17.

Column 32, Claim 4, lines 27-33:

"A recombinant gene of claim 7, wherein the DNA sequence is
   the structural gene sequence of FIG. 10, except that the initiation codon is ATG,
   a DNA sequence differing therefrom by codon degeneracy, or
   a DNA sequence hybridizable therewith."

should read:

--A recombinant gene of claim 1, wherein the DNA sequence is
   the structural gene sequence of FIG. 10, except that the initiation codon is ATG,
   a DNA sequence differing therefrom by codon degeneracy, or
   a DNA sequence hybridizable therewith or its complement, wherein the sequence or
     its complement codes for a polypeptide having said biological activity.--

This certificate supersedes the Certificate of Correction issued May 31, 2011.

Signed and Sealed this
Tenth Day of January, 2012

David J. Kappos
*Director of the United States Patent and Trademark Office*

UNITED STATES PATENT AND TRADEMARK OFFICE
CERTIFICATE OF CORRECTION

PATENT NO. : 6,153,401
APPLICATION NO. : 07/322604
DATED : November 28, 2000
INVENTOR(S) : Wolfgang R. Streber et al.

It is certified that error appears in the above-identified patent and that said Letters Patent is hereby corrected as shown below:

Please change column 2, line 25 as follows:

"The tfdA gene codes for ~~2,4-D monoamine oxygenase~~ 2,4-D monooxygenase,".

Please change column 23, line 58 as follows:

"at 420 nm. For the enzyme test of ~~2,4-D monooxigenase~~ 2,4-D monooxygenase".

Please change column 25, line 46 as follows:

"Accumulation of tfdA-Coded ~~2,4-D Monooxigenase~~ 2,4-D Monooxygenase,".

Signed and Sealed this
Twenty-seventh Day of March, 2012

David J. Kappos
*Director of the United States Patent and Trademark Office*